United States Patent
Gant et al.

(10) Patent No.: US 6,831,091 B2
(45) Date of Patent: Dec. 14, 2004

(54) SALT FORMS OF 3-(4-BROMO-2,6-DIFLUORO-BENZYLOXY)-5-[3-(4-PYRROLIDIN-1-YL-BUTYL)-UREIDO]-ISOTHIAZOLE-4-CARBOXYLIC ACID AMIDE AND METHOD OF PRODUCTION

(75) Inventors: Thomas George Gant, Niantic, CT (US); Glenn R. Williams, East Aurora, NY (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/993,640

(22) Filed: Nov. 27, 2001

(65) Prior Publication Data

US 2002/0151573 A1 Oct. 17, 2002

Related U.S. Application Data

(60) Provisional application No. 60/253,513, filed on Nov. 28, 2000.

(51) Int. Cl.⁷ .................. A61K 31/427; A61K 31/426; C07D 275/03; C07D 417/12; A61P 35/00
(52) U.S. Cl. ....................................... 514/372; 548/213
(58) Field of Search ........................... 548/213; 514/372

(56) References Cited

U.S. PATENT DOCUMENTS 6,235,764 B1 * 5/2001 Larson et al. ............... 514/372

* cited by examiner

Primary Examiner—Rita Desai
Assistant Examiner—Robert Shiao
(74) Attorney, Agent, or Firm—Peter C. Richardson; Krishna G. Banerjee; Garth Butterfield

(57) ABSTRACT

The invention relates to hydrochloride, hydrobromide, hemi-citrate, acetate, p-tosylate, L-tartrate, hemi-succinate, and mesylate salt forms of 3-(4-bromo-2,6-difluoro-benzyloxy)-5-[3-(4-pyrrolidin-1-yl-butyl)-ureido]-isothiazole-4-carboxylic acid amide having the following formula:

formula I

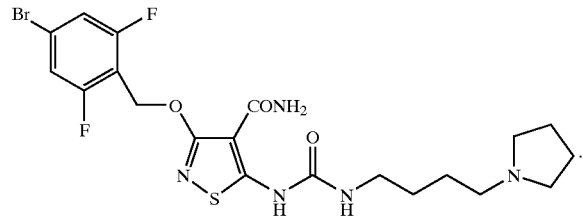

The invention also relates to pharmaceutical compositions containing the hydrochloride, hydrobromide, hemi-citrate, acetate, p-tosylate, L-tartrate, hemi-succinate, and mesylate salts of formula I. The invention further relates to methods of treating hyperproliferative diseases, such as cancers, in mammals, especially humans by administering the above salts and to methods of preparing the crystal forms of the above salts.

37 Claims, 9 Drawing Sheets

SALT FORMS OF 3-(4-BROMO-2,6-DIFLUORO-BENZYLOXY)-5-[3-(4-PYRROLIDIN-1-YL-BUTYL)-UREIDO]-ISOTHIAZOLE-4-CARBOXYLIC ACID AMIDE AND METHOD OF PRODUCTION

The application claims the benefit of U.S. Provisional Patent Application No. 60/253,513, filed Nov. 28, 2000, which is hereby incorporated by reference in its entirety.

BACKGROUND OF THE INVENTION

This invention relates to salt forms of 3-(4-bromo-2,6-difluoro-benzyloxy)-5-[3-(4-pyrrolidin-1-yl-butyl)-ureido]-isothiazole-4-carboxylic acid amide having the formula:

formula I

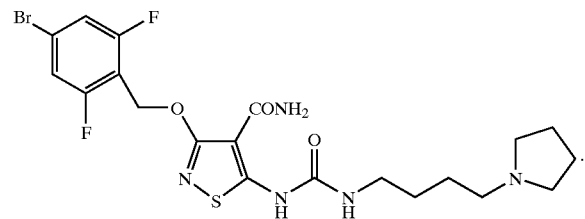

Formula I in its free base form is described in co-pending U.S. Ser. No. 09/316,837, filed May 21, 1999, the disclosure of which is hereby incorporated herein by reference in its entirety. The foregoing application is assigned in common with the present application. The free base of formula I is useful in the treatment of hyperproliferative diseases, such as cancers.

The present invention provides the hydrochloride, hydrobromide, hemi-citrate, acetate, p-tosylate, L-tartrate, hemi-succinate, and mesylate salt forms of 3-(4-bromo-2,6-difluoro-benzyloxy)-5-[3-(4-pyrrolidin-1-yl-butyl)-ureido]-isothiazole-4-carboxylic acid amide.

The present invention further relates to methods of making the hydrochloride, hydrobromide, hemi-citrate, acetate, p-tosylate, L-tartrate, hemi-succinate, and mesylate salt forms of 3-(4-bromo-2,6-difluoro-benzyloxy)-5-[3-(4-pyrrolidin-1-yl-butyl)-ureido]-isothiazole-4-carboxylic acid amide. The invention also relates to pharmaceutical compositions containing the hydrochloride, hydrobromide, hemi-citrate, acetate, p-tosylate, L-tartrate, hemi-succinate, and mesylate salts of the compound of formula I. The salts of the present invention are useful in the treatment of hyperproliferative diseases, such as cancers, in mammals, especially humans. The invention also relates to methods of administering the salts of formula I to treat hyperproliferative diseases.

Figure 1:
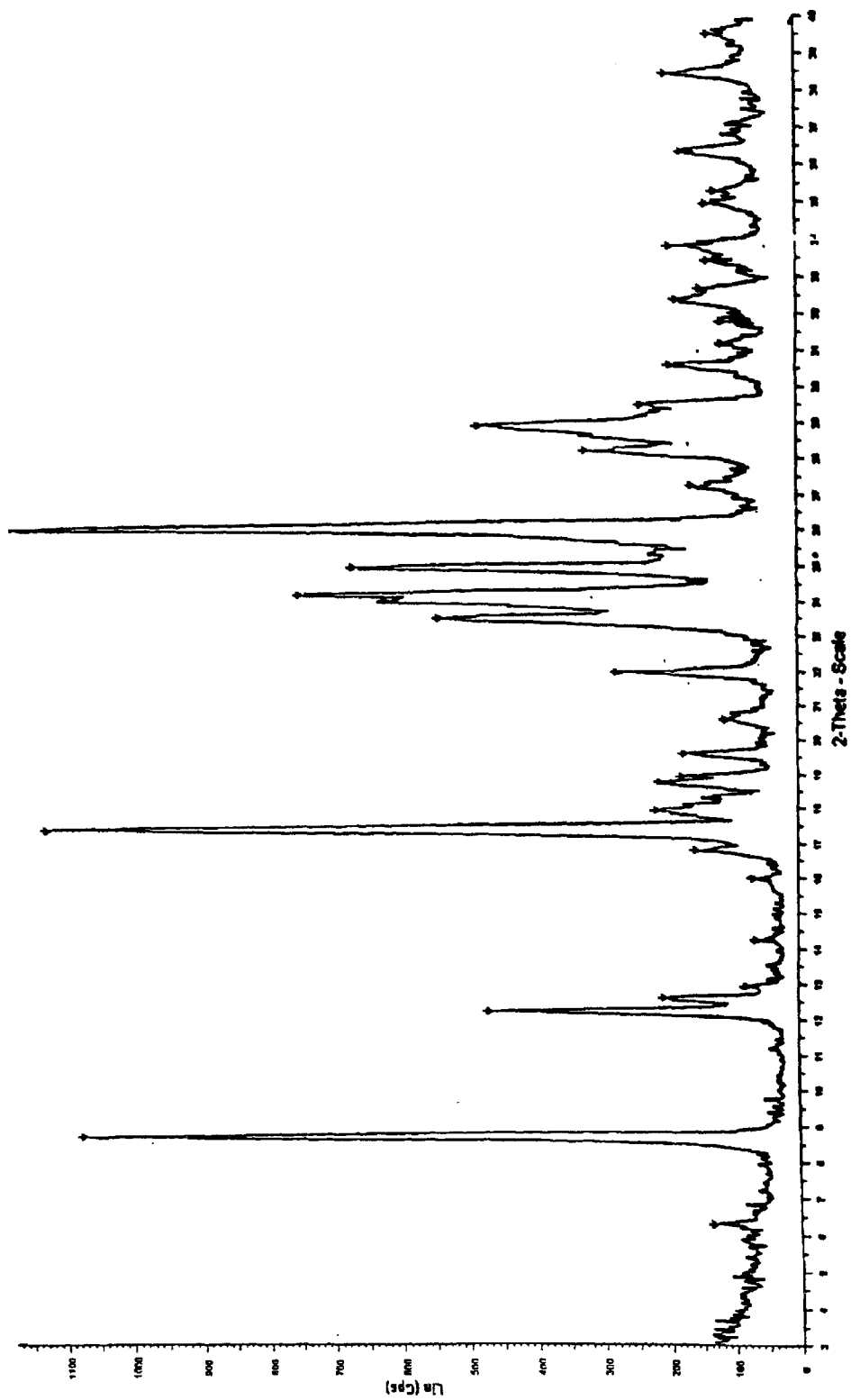
FIG. 1. is an X-ray powder diffraction spectrum of the of 3-(4-bromo-2,6-difluoro-benzyloxy)-5-[3-(4-pyrrolidin-1-yl-butyl)-ureido]-isothiazole-4-carboxylic acid amide hydrochloride which was prepared and isolated according to the process of the invention as illustrated in Example 2.
Figure 2:
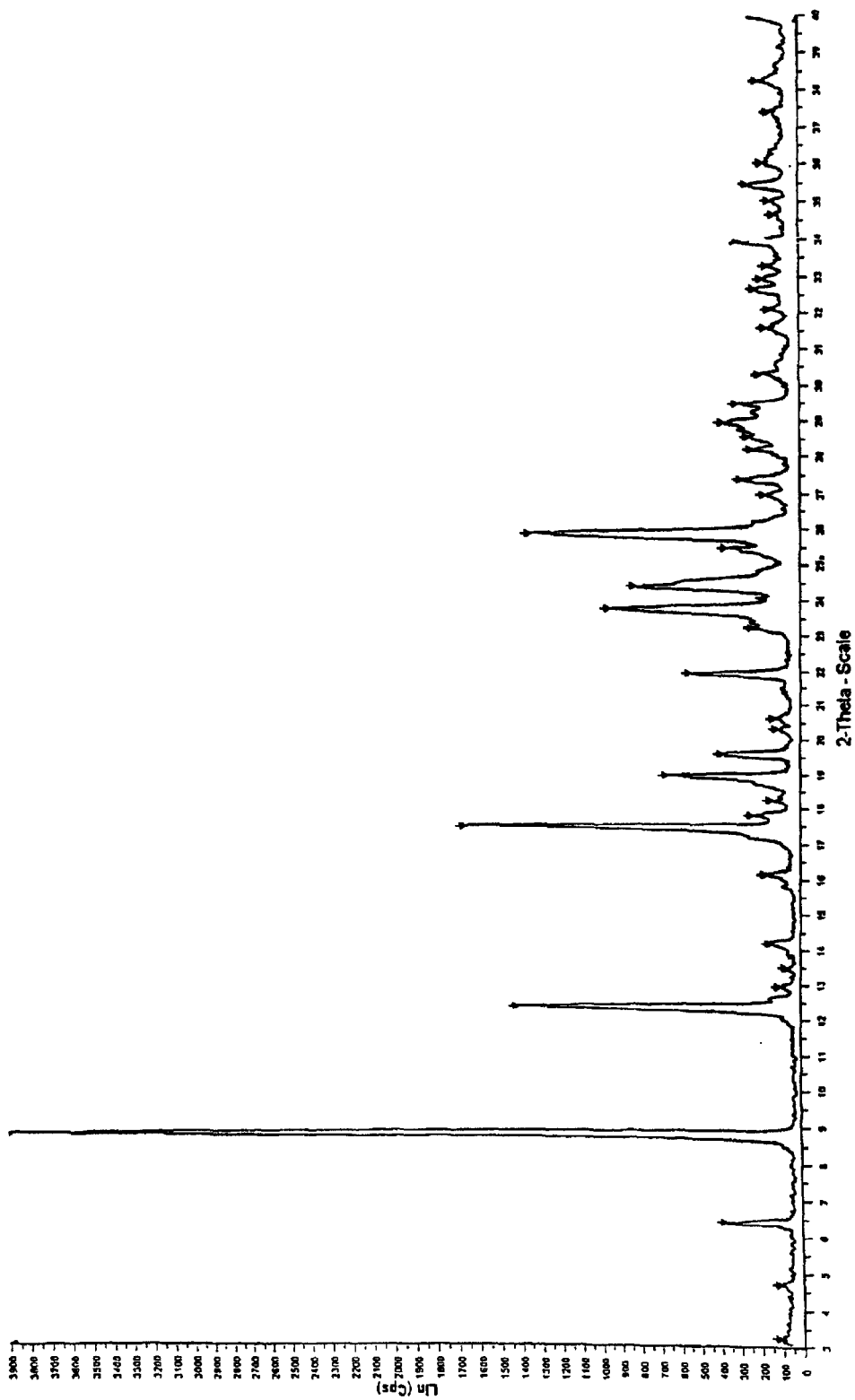
FIG. 2. is an X-ray powder diffraction spectrum of the of 3-(4-bromo-2,6-difluoro-benzyloxy)-5-[3-(4-pyrrolidin-1-yl-butyl)-ureido]-isothiazole-4-carboxylic acid amide hydrobromide which was prepared and isolated according to the process of the invention as illustrated in Example 3.
Figure 3:
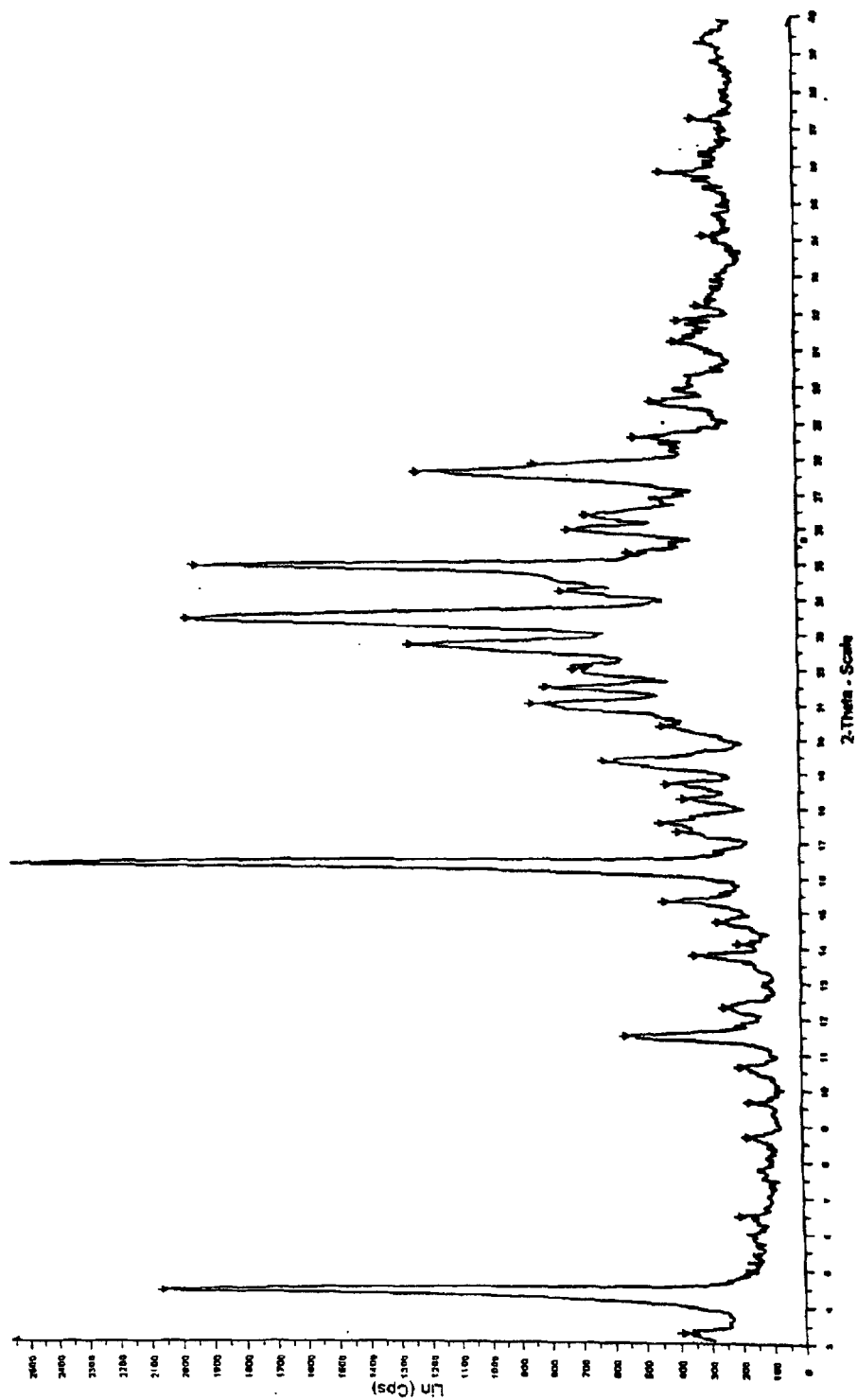
FIG. 3. is an X-ray powder diffraction spectrum of the of 3-(4-bromo-2,6-difluoro-benzyloxy)-5-[3-(4-pyrrolidin-1-yl-butyl)-ureido]-isothiazole-4-carboxylic acid amide hemi-citrate which was prepared and isolated according to the process of the invention as illustrated in Example 4.
Figure 4:
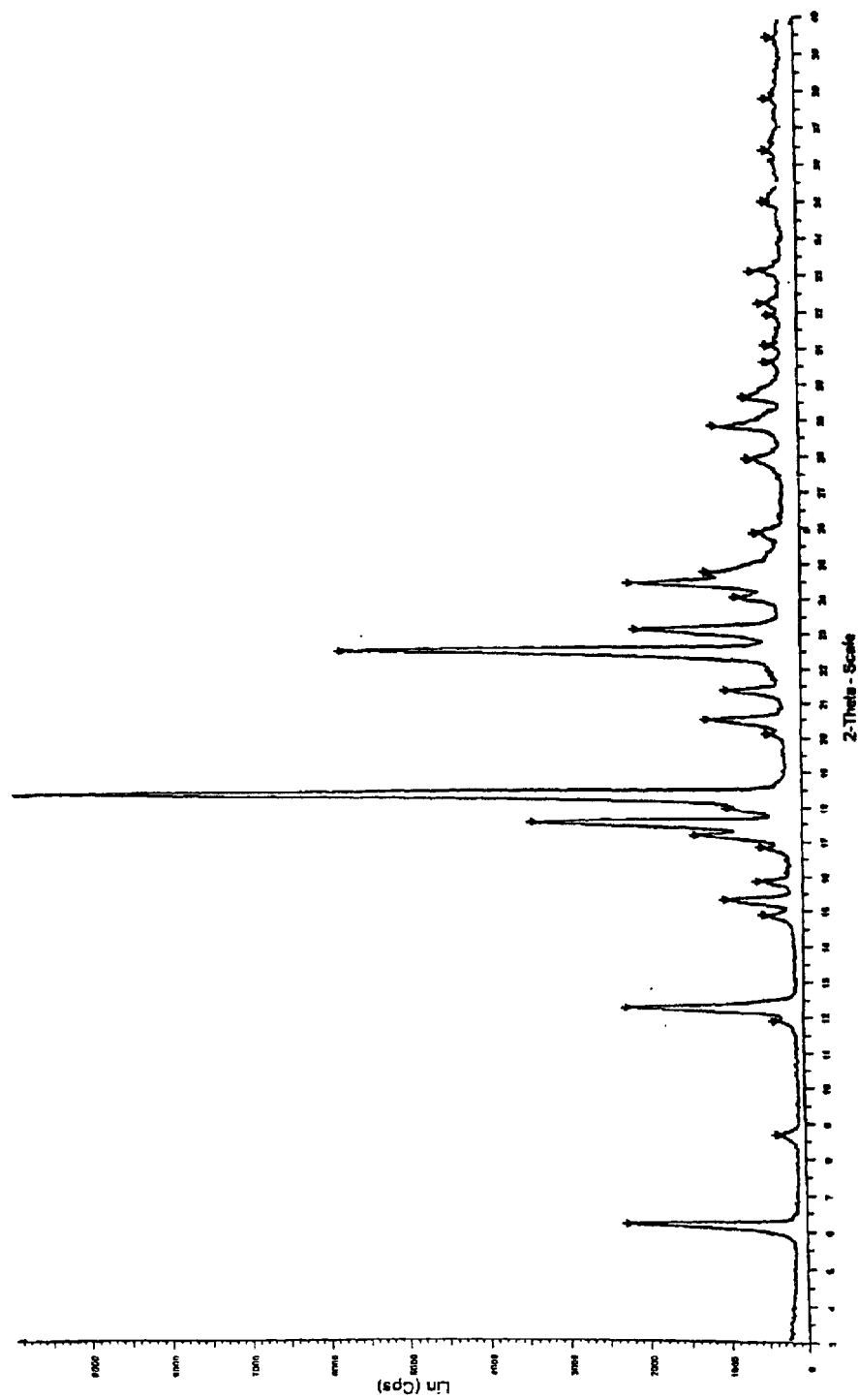
FIG. 4. is an X-ray powder diffraction spectrum of the of 3-(4-bromo-2,6-difluoro-benzyloxy)-5-[3-(4-pyrrolidin-1-yl-butyl)-ureido]-isothiazole-4-carboxylic acid amide acetate which was prepared and isolated according to the process of the invention as illustrated in Example 5.
Figure 5:
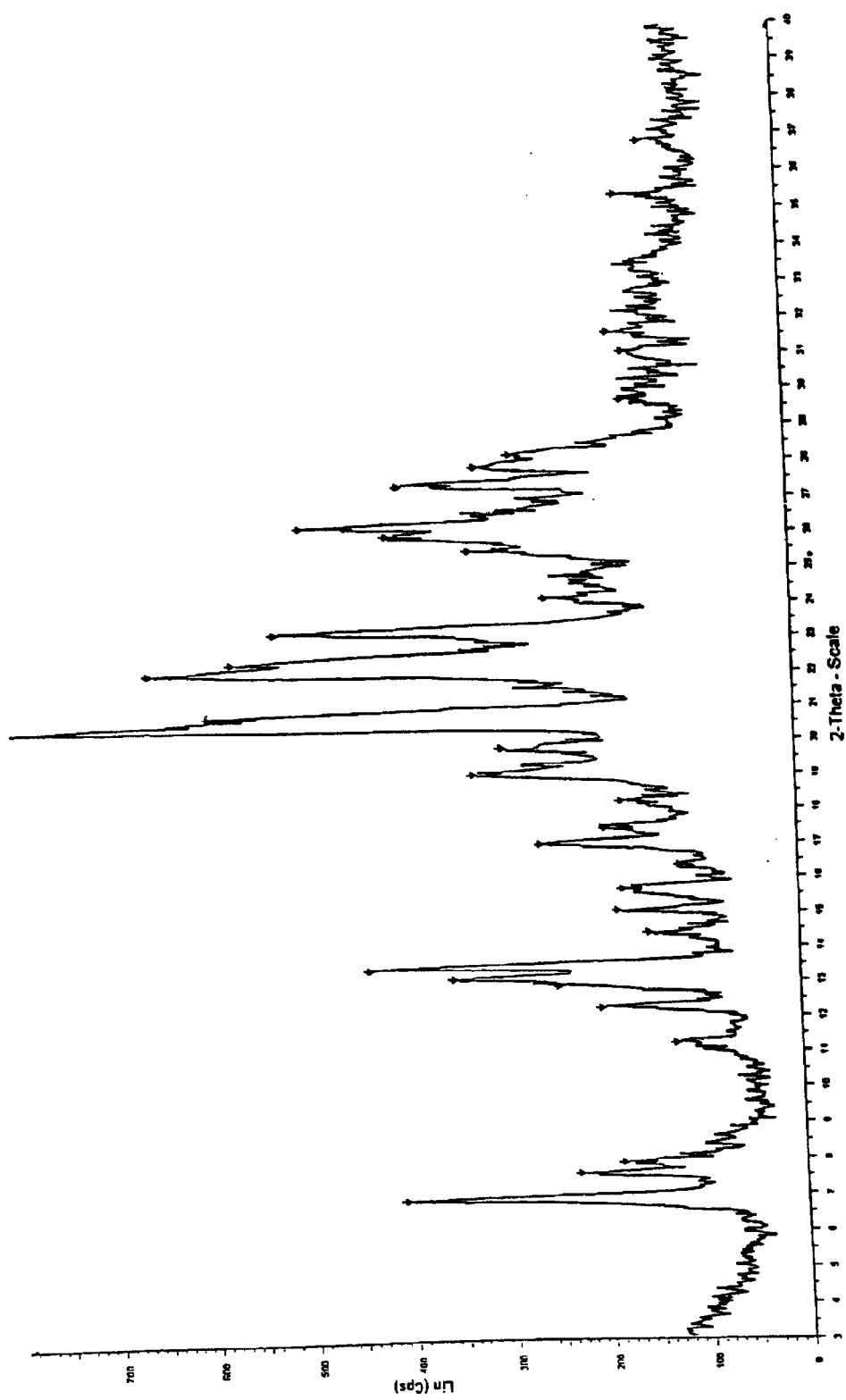
FIG. 5. is an X-ray powder diffraction spectrum of the of 3-(4-bromo-2,6-difluoro-benzyloxy)-5-[3-(4-pyrrolidin-1-yl-butyl)-ureido]-isothiazole-4-carboxylic acid amide p-tosylate which was prepared and isolated according to the process of the invention as illustrated in Example 6.

In the X-ray powder diffraction spectrums shown in FIGS. 1–9 the horizontal axis shows the angle of diffraction 2-theta degrees and the vertical axis shows the intensity of diffraction in Cps.

SUMMARY OF THE INVENTION

The present invention relates to hydrochloride, hydrobromide, hemi-citrate, acetate, p-tosylate, L-tartrate, hemi-succinate, and mesylate salt forms of 3-(4-bromo-2,6-difluoro-benzyloxy)-5-[3-(4-pyrrolidin-1-yl-butyl)-ureido]-isothiazole-4-carboxylic acid amide having the following formula:

formula I

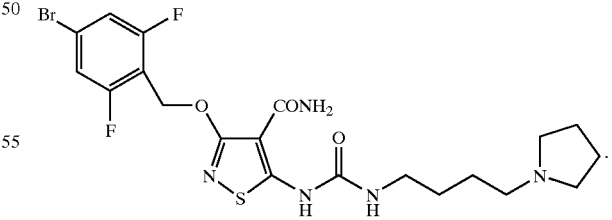

The present invention is also directed to processes for preparing the hydrochloride, hydrobromide, hemi-citrate, acetate, p-tosylate, L-tartrate, hemi-succinate, and mesylate salts of 3-(4-bromo-2,6-difluoro-benzyloxy)-5-[3-(4-pyrrolidin-1-yl-butyl)-ureido]-isothiazole-4-carboxylic acid amide comprising combining the free base with one of the aforementioned salts in the presence of a suitable organic solvent.

The hydrochloride, hydrobromide, hemi-citrate, acetate, p-tosylate, L-tartrate, hemi-succinate, and mesylate salts of 3-(4-bromo-2,6-difluoro-benzyloxy)-5-[3-(4-pyrrolidin-1-yl-butyl)-ureido]-isothiazole-4-carboxylic acid amide have been characterized by X-ray powder diffractometry.

The hydrochloride, hydrobromide, hemi-citrate, acetate, p-tosylate, L-tartrate, hemi-succinate (Forms A and B), and mesylate crystals of 3-(4-bromo-2,6-difluoro-benzyloxy)-5-[3-(4-pyrrolidin-1-yl-butyl)-ureido]-isothiazole-4-carboxylic acid amide provide powder X-ray diffraction spectrums substantially the same as the powder X-ray diffraction spectrums shown in FIGS. 1–9, respectively. However, it is known that a powder X-ray diffraction spectrum may be obtained with a measurement error depending on measurement conditions. In particular, it is generally known that intensities in a powder X-ray diffraction spectrum may fluctuate depending on measurement conditions. Therefore, it should be understood that the salts of the present invention are not limited to the crystals that provide X-ray powder diffraction spectrum completely identical to the X-ray powder diffraction spectrums shown in FIGS. 1–8, and that any crystals providing X-ray powder diffraction spectrums substantially the same as the aforementioned X-ray powder diffraction spectrums fall within the scope of the present invention. Those skilled in the field of X-ray powder diffractometry can readily judge the substantial identity of X-ray powder diffraction spectrums.

Generally, a measurement error of diffraction angle for an usual X-ray powder diffractometry is about 5% or less, and such degree of a measurement error should be taken into account as to diffraction angles. Furthermore, it should be understood that intensities may fluctuate depending on experimental conditions.

The hydrochloride salt form of the compound of formula I is characterized in that the crystal provides high-intensity diffraction peaks at diffraction angles of about 2-theta, [% relative intensity]: 8.623 [90.7], 12.121 [38.9], 17.298 [95.2], 23.397 [44.7], 23.944 [51.7], 24.119 [62.7], 24.873 [55.7], 25.948 [100], and 28.821 [39.6]. The hydrochloride salt form of the present invention provides a X-ray powder diffraction spectrum substantially the same as the X-ray diffraction spectrum shown in FIG. 1.

The characteristic 2-theta (2θ) values and relative intensity (RI) in percentage for the diffraction spectrum of the hydrochloride salt form of the compound of formula I is shown in Table 1.

TABLE 1

| 2θ | RI (%) |
|---|---|
| 6.225 | 10.5 |
| 8.623 | 90.7 |
| 12.121 | 38.9 |
| 12.522 | 16.8 |
| 12.873 | 6.0 |
| 14.206 | 4.7 |
| 15.951 | 5.1 |
| 16.736 | 12.4 |
| 17.298 | 95.2 |
| 17.868 | 17.6 |
| 18.712 | 17.1 |
| 18.880 | 14.2 |
| 19.549 | 13.8 |
| 20.552 | 8.5 |
| 21.896 | 22.2 |
| 23.397 | 44.7 |
| 23.944 | 51.7 |
| 24.119 | 62.7 |

TABLE 1-continued

| 2θ | RI (%) |
|---|---|
| 24.873 | 55.7 |
| 25.948 | 100.0 |
| 27.216 | 12.6 |
| 28.146 | 6.0 |
| 28.821 | 39.6 |
| 29.438 | 19.0 |
| 30.543 | 15.3 |
| 31.144 | 8.7 |
| 31.757 | 8.7 |
| 32.348 | 14.6 |
| 32.640 | 11.4 |
| 33.407 | 10.4 |
| 33.778 | 15.3 |
| 34.920 | 10.5 |
| 35.273 | 9.4 |
| 36.321 | 13.6 |
| 38.409 | 15.5 |
| 39.500 | 9.9 |

The hydrobromide salt form of the compound of formula I is characterized in that the crystal provides high-intensity diffraction peaks at diffraction angles of about 2-theta, [% relative intensity]: 8.687 [100.0], 12.264 [35.9], 17.374 [42.3], 23.711 [24.0], 24.335 [20.7], and 25.769 [34.3]. The hydrobromide salt form of the present invention provides a X-ray powder diffraction spectrum substantially the same as the X-ray diffraction spectrum shown in FIG. 2.

The characteristic 2-theta (2θ) values and relative intensity (%) for the diffraction spectrum of the hydrobromide salt form of the compound of formula I is shown below in Table 2.

TABLE 2

| 2θ | RI (%) |
|---|---|
| 3.156 | 2.5 |
| 4.615 | 2.4 |
| 6.331 | 9.3 |
| 8.687 | 100.0 |
| 12.264 | 35.9 |
| 12.890 | 2.2 |
| 13.445 | 1.4 |
| 14.140 | 3.4 |
| 16.083 | 4.0 |
| 17.374 | 42.3 |
| 17.767 | 5.6 |
| 18.185 | 3.2 |
| 18.913 | 16.6 |
| 19.528 | 9.5 |
| 20.286 | 2.5 |
| 20.581 | 2.9 |
| 21.874 | 13.6 |
| 23.188 | 5.6 |
| 23.711 | 24.0 |
| 24.335 | 20.7 |
| 25.435 | 9.1 |
| 25.769 | 34.3 |
| 26.940 | 4.1 |
| 27.345 | 7.0 |
| 28.160 | 5.7 |
| 28.528 | 6.1 |
| 28.916 | 9.4 |
| 29.418 | 7.7 |
| 30.266 | 4.6 |
| 31.561 | 3.9 |
| 32.082 | 3.4 |
| 32.638 | 5.3 |
| 32.925 | 4.4 |
| 33.256 | 3.7 |
| 33.897 | 7.9 |
| 34.628 | 2.8 |

TABLE 2-continued

| 2θ | RI (%) |
|---|---|
| 34.999 | 3.3 |
| 35.432 | 6.1 |
| 36.006 | 4.3 |
| 37.361 | 3.4 |
| 38.224 | 4.8 |

The hemi-citrate salt form of the compound of formula I is characterized in that the crystal provides high-intensity diffraction peaks at diffraction angles of about 2-theta, [% relative intensity]: 4.306 [79.9], 16.317 [100.0], 20.988 [32.7], 21.476 [30.9], 22.643 [48.7], 23.384 [76.9], 24.891 [76.0], 27.573 [47.9], and 27.840 [32.3]. The hemi-citrate salt form of the present invention provides a X-ray powder diffraction spectrum substantially the same as the X-ray diffraction spectrum shown in FIG. 3.

The characteristic 2-theta (2θ) values and relative intensity (%) for the diffraction spectrum of the hemi-citrate salt form of the compound of formula I is shown below in Table 3.

TABLE 3

| 2θ | RI (%) |
|---|---|
| 3.201 | 14.3 |
| 4.306 | 79.9 |
| 6.429 | 7.0 |
| 8.620 | 6.0 |
| 9.589 | 5.6 |
| 10.583 | 6.8 |
| 11.449 | 20.9 |
| 12.300 | 8.7 |
| 13.766 | 12.4 |
| 14.086 | 7.0 |
| 14.710 | 9.5 |
| 15.297 | 16.0 |
| 16.317 | 100.0 |
| 17.309 | 14.4 |
| 17.572 | 16.5 |
| 18.258 | 13.7 |
| 18.693 | 15.8 |
| 19.344 | 23.4 |
| 20.394 | 16.4 |
| 20.988 | 32.7 |
| 21.476 | 30.9 |
| 21.994 | 27.3 |
| 22.643 | 48.7 |
| 23.384 | 76.9 |
| 24.217 | 28.8 |
| 24.891 | 76.0 |
| 25.320 | 20.4 |
| 25.948 | 28.0 |
| 26.370 | 25.7 |
| 27.573 | 47.9 |
| 27.840 | 32.3 |
| 28.609 | 19.6 |
| 29.630 | 17.4 |
| 31.251 | 14.6 |
| 31.848 | 14.2 |
| 32.235 | 11.8 |
| 34.147 | 11.0 |
| 35.878 | 16.2 |
| 37.337 | 12.3 |

The acetate salt form of the compound of formula I is characterized in that the crystal provides high-intensity diffraction peaks at diffraction angles of about 2-theta, [% relative intensity]: 6.096 [21.7], 12.183 [21.4], 17.451 [33.3], 18.288 [100.0], 22.441 [57.7], 23.086 [19.9], and 24.439 [20.7]. The acetate salt form of the present invention provides a X-ray powder diffraction spectrum substantially the same as the X-ray diffraction spectrum shown in FIG. 4.

The characteristic 2-theta (2θ) values and relative intensity (%) for the diffraction spectrum of the acetate salt form of the compound of formula I is shown below in Table 4.

TABLE 4

| 2θ | RI (%) |
|---|---|
| 6.096 | 21.7 |
| 8.625 | 2.8 |
| 11.840 | 2.9 |
| 12.183 | 21.4 |
| 14.836 | 4.2 |
| 15.264 | 9.2 |
| 15.824 | 5.0 |
| 16.793 | 4.5 |
| 17.121 | 12.8 |
| 17.451 | 33.3 |
| 17.920 | 8.7 |
| 18.288 | 100.0 |
| 20.088 | 3.6 |
| 20.458 | 11.3 |
| 21.346 | 8.9 |
| 22.441 | 57.7 |
| 23.086 | 19.9 |
| 24.038 | 7.5 |
| 24.439 | 20.7 |
| 24.760 | 11.3 |
| 25.861 | 5.0 |
| 27.930 | 5.8 |
| 28.820 | 10.0 |
| 29.648 | 6.1 |
| 30.634 | 3.3 |
| 31.112 | 3.2 |
| 31.951 | 2.9 |
| 32.271 | 4.1 |
| 33.127 | 5.1 |
| 35.030 | 3.4 |
| 36.445 | 3.2 |
| 37.830 | 3.0 |
| 39.478 | 2.5 |

The p-tosylate salt form of the compound of formula I is characterized in that the crystal provides high-intensity diffraction peaks at diffraction angles of about 2-theta, [% relative intensity]: 20.446 [100.0], 20.760 [74.0], 22.092 [81.7], 22.371 [70.8], 23.190 [65.2], and 26.239 [61.5]. The p-tosylate salt form of the present invention provides a X-ray powder diffraction spectrum substantially the same as the X-ray diffraction spectrum shown in FIG. 5.

The characteristic 2-theta (2θ) values and relative intensity (%) for the diffraction spectrum of the p-tosylate salt form of the compound of formula I is shown below in Table 5.

TABLE 5

| 2θ | RI (%) |
|---|---|
| 6.817 | 50.3 |
| 7.515 | 28.0 |
| 7.822 | 22.3 |
| 11.157 | 15.0 |
| 12.205 | 24.5 |
| 12.800 | 30.0 |
| 13.047 | 43.6 |
| 13.373 | 53.9 |
| 14.337 | 18.3 |
| 15.001 | 22.2 |
| 15.601 | 21.4 |
| 16.297 | 14.0 |
| 16.943 | 32.0 |
| 17.362 | 23.5 |
| 18.174 | 21.3 |
| 18.976 | 40.4 |
| 19.739 | 36.7 |
| 20.446 | 100.0 |

TABLE 5-continued

| 2θ | RI (%) |
|---|---|
| 20.760 | 74.0 |
| 22.092 | 81.7 |
| 22.371 | 70.8 |
| 23.190 | 65.2 |
| 24.110 | 30.5 |
| 25.471 | 40.2 |
| 25.932 | 50.4 |
| 26.239 | 61.5 |
| 27.355 | 48.8 |
| 27.833 | 39.0 |
| 28.167 | 34.5 |
| 29.672 | 19.6 |
| 31.038 | 19.3 |
| 31.586 | 21.2 |
| 35.357 | 19.6 |
| 36.800 | 16.4 |

The L-tartrate salt form of the compound of formula I is characterized in that the crystal provides high-intensity diffraction peaks at diffraction angles of about 2-theta, [% relative intensity]: 4.061 [82.9], 20.821 [85.6], 21.634 [100.0], 22.179 [94.0], and 25.858 [95.1].

Figure 6:
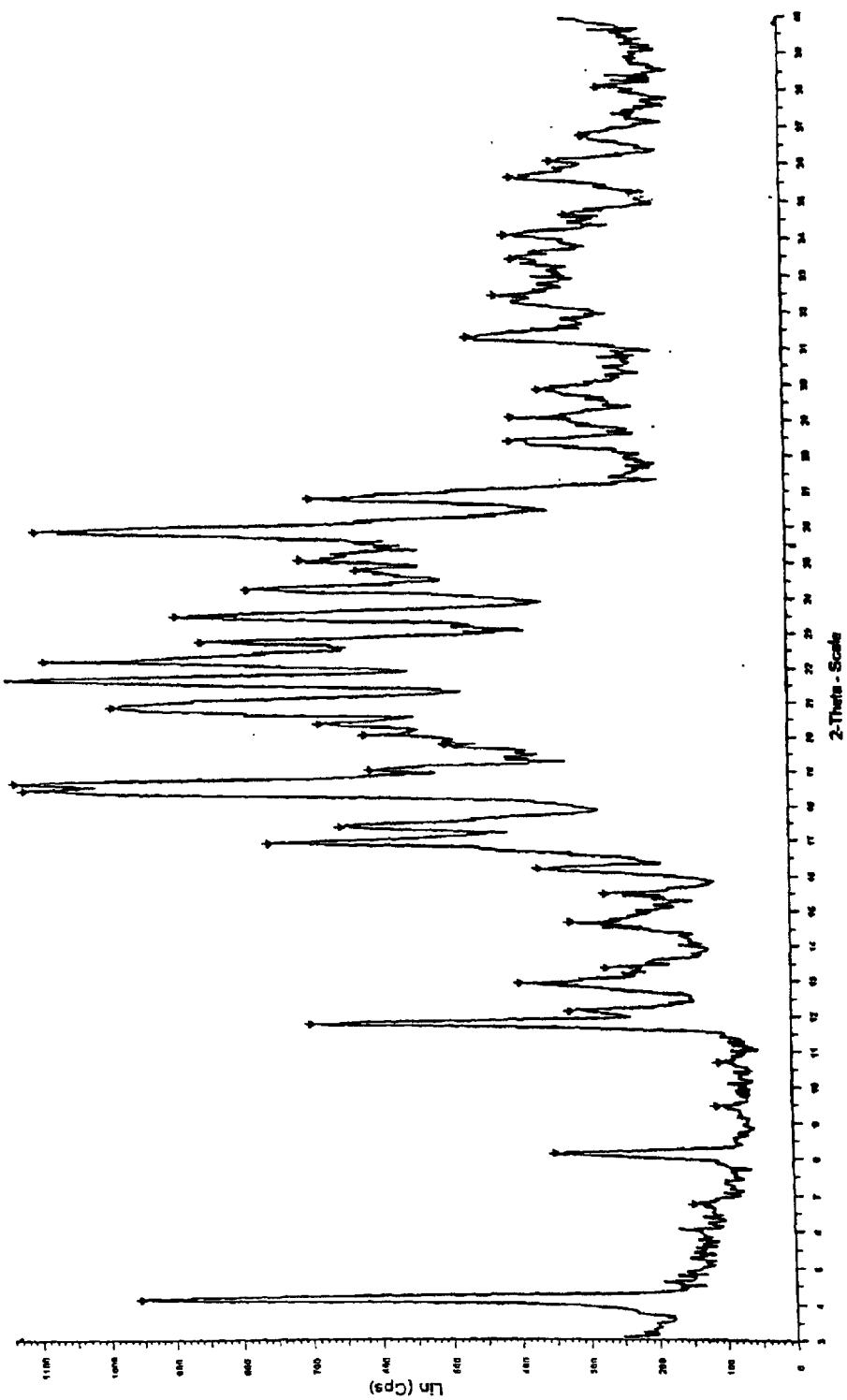
FIG. 6. is an X-ray powder diffraction spectrum of the of 3-(4-bromo-2,6-difluoro-benzyloxy)-5-[3-(4-pyrrolidin-1-yl-butyl)-ureido]-isothiazole-4-carboxylic acid amide L-tartrate which was prepared and isolated according to the process of the invention as illustrated in Example 7.
Figure 7:
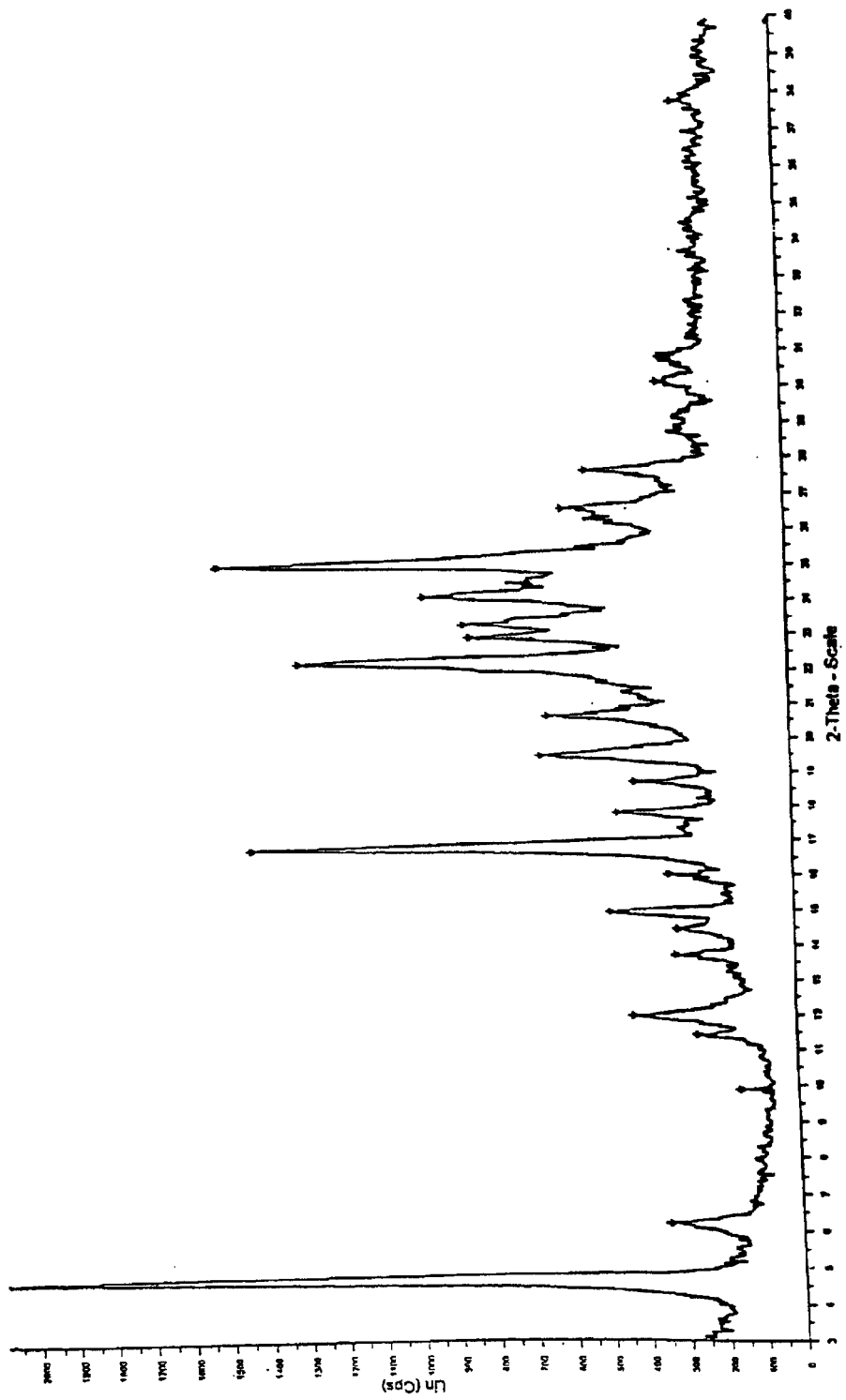
FIG. 7. is an X-ray powder diffraction spectrum of the of 3-(4-bromo-2,6-difluoro-benzyloxy)-5-[3-(4-pyrrolidin-1-yl-butyl)-ureido]-isothiazole-4-carboxylic acid amide hemi-succinate, identified as From A hemi-succinate, which was prepared and isolated according to the process of the invention as illustrated in Example 8.
Figure 8:
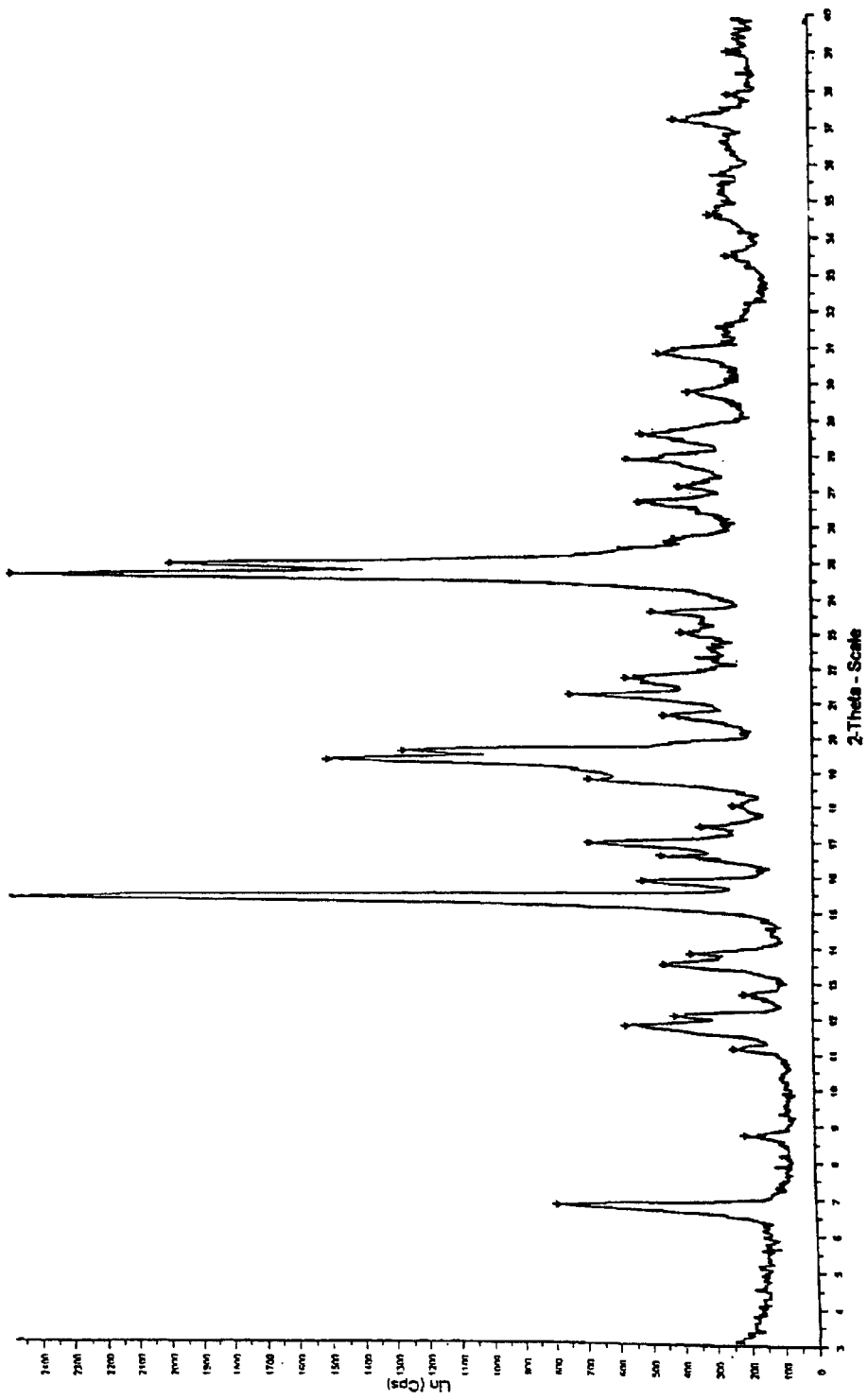
FIG. 8. is an X-ray powder diffraction spectrum of the of 3-(4-bromo-2,6-difluoro-benzyloxy)-5-[3-(4-pyrrolidin-1-yl-butyl)-ureido]-isothiazole-4-carboxylic acid amide hemi-succinate, identified as Form B, which was prepared and isolated according to the process of the invention as illustrated in Example 9.
Figure 9:
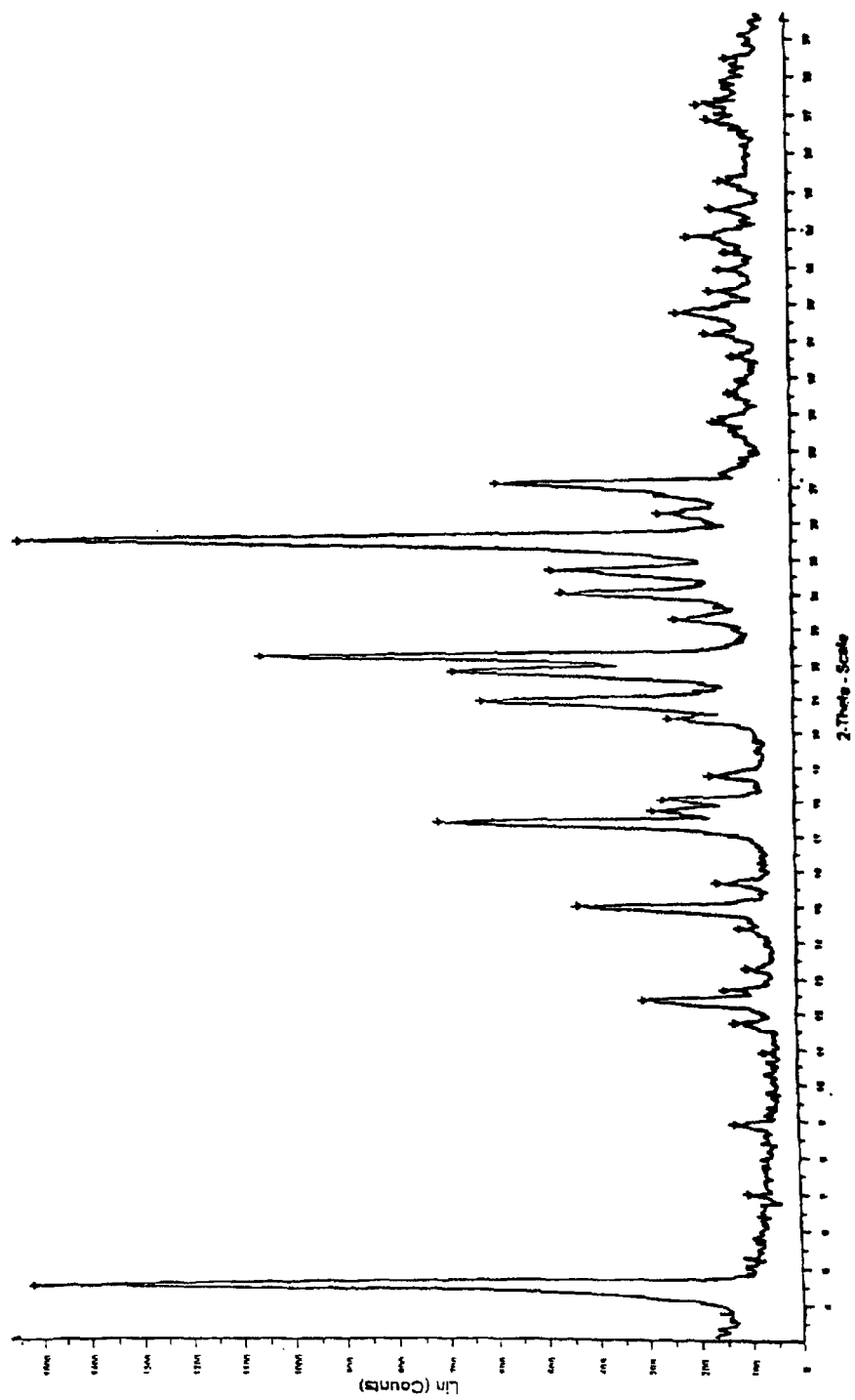
FIG. 9. is an X-ray powder diffraction spectrum of the of 3-(4-bromo-2,6-difluoro-benzyloxy)-5-[3-(4-pyrrolidin-1-yl-butyl)-ureido]-isothiazole-4-carboxylic acid amide mesylate which was prepared and isolated according to the process of the invention as illustrated in Example 10.

The L-tartrate salt form of the present invention provides a X-ray powder diffraction spectrum substantially the same as the X-ray diffraction spectrum shown in FIG. 6.

The characteristic 2-theta (2θ) values and relative intensity (%) for the diffraction spectrum of the L-tartrate salt form of the compound of formula I is shown below in Table 6.

TABLE 6

| 2θ | RI (%) |
|---|---|
| 4.061 | 82.9 |
| 6.678 | 11.8 |
| 8.057 | 29.4 |
| 9.383 | 8.7 |
| 10.647 | 8.3 |
| 11.711 | 60.2 |
| 12.075 | 27.4 |
| 12.868 | 33.8 |
| 13.320 | 22.7 |
| 14.631 | 27.2 |
| 15.428 | 22.7 |
| 16.143 | 31.2 |
| 16.853 | 65.3 |
| 17.338 | 56.2 |
| 18.400 | 97.0 |
| 18.639 | 98.2 |
| 18.994 | 52.4 |
| 19.722 | 42.9 |
| 20.010 | 53.0 |
| 20.334 | 58.7 |
| 20.821 | 85.6 |
| 21.634 | 100.0 |
| 22.179 | 94.0 |
| 22.730 | 73.8 |
| 23.477 | 77.1 |
| 24.257 | 67.8 |
| 24.788 | 53.8 |
| 25.081 | 60.9 |
| 25.858 | 95.1 |
| 26.803 | 59.6 |
| 28.386 | 34.3 |
| 29.067 | 34.1 |
| 29.844 | 30.5 |
| 31.309 | 39.4 |
| 32.465 | 36.1 |
| 33.442 | 33.7 |
| 34.090 | 34.6 |
| 34.642 | 26.8 |

TABLE 6-continued

| 2θ | RI (%) |
|---|---|
| 35.635 | 33.7 |
| 36.073 | 28.5 |
| 36.771 | 24.5 |
| 38.080 | 22.6 |

The anhydride hemi-succinate crystals of 3-(4-bromo-2,6-difluoro-benzyloxy)-5-[3-(4-pyrrolidin-1-yl-butyl)-ureido]-isothiazole-4-carboxylic acid amide were found to have hygroscopic properties at humidity conditions of 90%. Two crystal forms of hemi-succinate crystals of 3-(4-bromo-2,6-difluoro-benzyloxy)-5-[3-(4-pyrrolidin-1-yl-butyl)-ureido]-isothiazole-4-carboxylic acid amide were identified. Hemi-succinate crystal form A of the compound of formula I was found to have a 0.6% w/w hygroscopicity at 30° C. and 90% RH. Hemi-succinate crystal form B of the compound of formula I was found to have a 1.5% w/w hygroscopicity at 30° C. and 90% RH. Hemi-succinate form B is converted into the hemi-succinate form A in refluxing ethanol in less than 24 hours. Hemi-succinate salt forms A and B of the present invention provide X-ray powder diffraction spectrums substantially the same as the X-ray diffraction spectrums shown in FIGS. 7 and 8, respectively.

The hemi-succinate salt form A of the compound of formula I is characterized in that the crystal provides high-intensity diffraction peaks at diffraction angles of about 2-theta, [% relative intensity]: 4.634 [100.0], 16.735 [67.2], 22.179 [60.8], and 25.002 [70.3].

The hemi-succinate salt form B of the compound of formula I is characterized in that the crystal provides high-intensity diffraction peaks at diffraction angles of about 2-theta, [% relative intensity]: 6.714 [31.0], 15.272 [100.0], 19.197 [59.3], 19.457 [50.0], 24.487 [99.0], and 24.802 [79.1].

The characteristic 2-theta (2θ) values and relative intensity (%) for the diffraction spectrums of hemi-succinate salt forms A and B of the compound of formula I are shown below in Tables 7 and 8, respectively.

TABLE 7

| 2θ | RI (%) |
|---|---|
| 4.634 | 100.0 |
| 6.149 | 15.5 |
| 9.843 | 6.2 |
| 11.392 | 11.3 |
| 11.937 | 19.2 |
| 13.683 | 13.8 |
| 14.440 | 13.5 |
| 14.896 | 21.9 |
| 15.996 | 14.4 |
| 16.735 | 67.2 |
| 17.760 | 20.6 |
| 18.679 | 18.4 |
| 19.421 | 30.2 |
| 20.586 | 29.2 |
| 22.179 | 60.8 |
| 22.866 | 38.7 |
| 23.255 | 39.5 |
| 24.079 | 44.6 |
| 25.002 | 70.3 |
| 26.549 | 26.8 |
| 27.609 | 23.7 |
| 30.106 | 14.3 |
| 30.797 | 13.7 |
| 37.769 | 11.4 |

TABLE 8

| 2θ | RI (%) |
|---|---|
| 6.714 | 31.0 |
| 8.666 | 7.3 |
| 11.092 | 8.6 |
| 11.696 | 21.9 |
| 12.008 | 15.9 |
| 12.630 | 7.3 |
| 13.466 | 17.2 |
| 13.774 | 13.9 |
| 15.272 | 100.0 |
| 15.813 | 19.8 |
| 16.551 | 17.5 |
| 16.875 | 26.4 |
| 17.365 | 12.6 |
| 17.986 | 8.6 |
| 18.710 | 26.4 |
| 19.197 | 59.3 |
| 19.457 | 50.0 |
| 20.597 | 17.2 |
| 21.160 | 28.8 |
| 21.648 | 21.7 |
| 22.988 | 15.0 |
| 23.568 | 18.6 |
| 24.487 | 99.0 |
| 24.802 | 79.1 |
| 25.640 | 15.9 |
| 26.641 | 20.1 |
| 27.090 | 15.1 |
| 27.843 | 21.5 |
| 28.552 | 19.7 |
| 29.732 | 14.1 |
| 30.796 | 17.5 |
| 33.484 | 9.4 |
| 34.594 | 11.4 |
| 37.212 | 15.5 |
| 37.905 | 8.9 |
| 39.023 | 8.9 |

The mesylate salt form of the compound of formula I is characterized in that the crystal provides high-intensity diffraction peaks at diffraction angles of about 2-theta, [% relative intensity]: 4.417 [99.3], 17.288 [45.5], 20.828 [39.6], 21.677 [43.5], 22.148 [68.3], 25.427 [100.0], and 27.006 [37.5]. The mesylate salt form of the present invention provides a X-ray powder diffraction spectrum substantially the same as the X-ray diffraction spectrum shown in FIG. 9.

The characteristic 2-theta (2θ) values and relative intensity (%) for the diffraction spectrum of the mesylate salt form of the compound of formula I is shown below in Table 9.

TABLE 9

| 2θ | RI (%) |
|---|---|
| 4.417 | 99.3 |
| 8.806 | 7.2 |
| 11.664 | 7.0 |
| 12.267 | 18.7 |
| 12.610 | 8.3 |
| 13.224 | 5.4 |
| 14.915 | 27.1 |
| 15.619 | 9.1 |
| 17.288 | 45.5 |
| 17.654 | 17.2 |
| 17.993 | 15.9 |
| 18.728 | 9.8 |
| 20.358 | 15.0 |
| 20.828 | 39.6 |
| 21.677 | 43.5 |
| 22.148 | 68.3 |
| 23.231 | 14.1 |
| 23.966 | 28.8 |
| 24.602 | 30.2 |
| 25.427 | 100.0 |
| 26.226 | 16.1 |
| 27.006 | 37.5 |
| 28.757 | 8.8 |
| 29.564 | 6.7 |
| 30.560 | 6.2 |
| 31.173 | 9.7 |
| 31.722 | 13.3 |
| 32.337 | 9.0 |
| 32.940 | 7.8 |
| 33.796 | 11.8 |
| 34.550 | 8.7 |
| 35.308 | 7.6 |
| 36.883 | 9.1 |

X-ray powder diffraction pattern is only one of many ways to characterize the arrangement of atoms comprising the salts of 3-(4-bromo-2,6-difluoro-benzyloxy)-5-[3-(4-pyrrolidin-1-yl-butyl)-ureido]-isothiazole-4-carboxylic acid amide. Other methods are well known in the art, such as, single X-ray crystal diffraction, may be used to identify aforementioned salt forms of formula I.

It has unexpectedly been found that the acetate, hydrochloride, hydrobromide, hemi-succinate, and mesylate salt forms of the compound of formula I have high crystallinity, i.e., substantially free of amorphous material. Such salts have the advantage that they provide more reproducible dosing results. The hydrochloride, hydrobromide, and hemi-succinate salt forms of the compound of formula I are substantially hygroscopically stable, which alleviates potential problems associated with weight changes of the active ingredient during the manufacture of capsules or tablets. The hydrochloride and hydrobromide forms of the compound of formula I have the additional advantage that they have a low tendency for concentrated aqueous solution to form viscous mixtures upon standing. Furthermore, the hydrobromide salt form of the compound of formula I delivers a mild sedative effect at low to moderate dosing. The mesylate salt form of the compound of formula I has rapid kinetic aqueous solubility which simplifies aqueous dosing and makes it suitable for injectable dosage forms. Furthermore, the mesylate salt form of the compound of formula I with enhanced solubility characteristics facilitates the dissolution of solid dosage forms in a timely manner.

The p-tosylate, L-tartrate and hemi-citrate salts have greater kinetic solubility than the free base or hydrochloride form of the compound of formula I. Additionally, the p-tosylate, L-tartrate, and hemi-citrate salts of the compound of formula I are less hygroscopic than the mesylate salt of the compound of formula I. Accordingly, the p-tosylate, L-tartrate, and hemi-citrate salts of the compound of formula I are more stable in air and can be used without deliquescence.

The invention also relates to a pharmaceutical composition for the treatment of a hyperproliferative disorder in a mammal, which comprises a therapeutically effective amount of a salt of a compound of formula I or a hydrate thereof, and a pharmaceutically acceptable carrier. In one embodiment, said pharmaceutical composition is for the treatment of cancer such as brain, lung, squamous cell, bladder, gastric, pancreatic, breast, head, neck, renal, prostate, colorectal, oesophageal, gynecological (such as ovarian) or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertrophy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a salt of a compound of formula I or hydrate thereof, and a pharmaceutically acceptable carrier.

The invention also relates to a pharmaceutical composition for the prevention of blastocyte implantation in a mammal which comprises a therapeutically effective amount of a salt of a compound of formula I or hydrate thereof, and a pharmaceutically acceptable carrier.

The invention also relates to a pharmaceutical composition for treating a disease related to vasculogenesis or angiogenesis in a mammal which comprises a therapeutically effective amount of a salt of a compound of formula I or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of a salt of a compound of formula I or hydrate thereof. In one embodiment, said method relates to the treatment of cancer such as brain, squamous cell, bladder, gastric, pancreatic, breast, head, neck, oesophageal, prostate, colorectal, lung, renal, gynecological (such as ovarian) or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a salt of a compound of formula I or hydrate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method of treating pancreatitis or kidney disease in a mammal which comprises administering to said mammal a therapeutically effective amount of a salt of a compound of formula I or hydrate thereof.

The invention also relates to a method of preventing blastocyte implantation in a mammal which comprises administering to said mammal a therapeutically effective amount of a salt of a compound of formula I or hydrate thereof.

The invention also relates to a method of treating diseases related to vasculogenesis or angiogenesis in a mammal which comprises administering to said mammal an effective amount of a salt of a compound of formula I or hydrate thereof. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, macular degeneration, hemangioma, glioma, melanoma, Kaposi's sarcoma and ovarian, breast, lung, pancreatic, prostate, colon and epidermoid cancer.

Further the compounds of the present invention may be used as a contraceptive in mammals. In one preferred embodiment the compounds of the present invention may be used to prevent pregnancy in a female mammal.

Patients that can be treated with the salts of formula I and hydrates of said compounds, according to the methods of this invention include, for example, patients that have been diagnosed as having psoriasis, BPH, lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a pharmaceutical composition for the treatment of an infection in a mammal, including a human, that is facilitated by farnesyl protein transferase, such as malaria or hepatitus delta virus, comprising an amount of a salt of a compound of the formula I, as defined above, a prodrug or solvate thereof, that is effective in treating abnormal cell growth, and a pharmaceutically acceptable carrier.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs; and (4) any tumors that proliferate by virtue of farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

DETAILED DESCRIPTION OF THE INVENTION

The present invention relates to hydrochloride, hydrobromide, hemi-citrate, acetate, p-tosylate, L-tartrate, hemi-succinate, and mesylate salts of 3-(4-bromo-2,6-difluoro-benzyloxy)-5-[3-(4-pyrrolidin-1-yl-butyl)-ureido]-isothiazole-4-carboxylic acid amide.

The invention further relates to a method making the hydrochloride, hydrobromide, hemi-citrate, acetate, p-tosylate, L-tartrate, hemi-succinate, and mesylate salts of 3-(4-bromo-2,6-difluoro-benzyloxy)-5-[3-(4-pyrrolidin-1-yl-butyl)-ureido]-isothiazole-4-carboxylic acid amide. The salt forms of the present invention are useful in the treatment of hyperproliferative diseases, such as cancers, in mammals, especially humans, and to pharmaceutical compositions containing such compounds.

The salt forms of the compound of formula I have been characterized using X-ray powder diffractometry. The hydrochloride, hydrobromide, hemi-citrate, acetate, p-tosylate, L-tartrate, hemi-succinate (Form A), hemi-succinate (Form B) and mesylate salts of the compound of formula I provide X-ray powder diffraction patterns substantially the same as shown in FIGS. 1–9.

The hydrochloride salt of 3-(4-bromo-2,6-difluoro-benzyloxy)-5-[3-(4-pyrrolidin-1-yl-butyl)-ureido]-isothiazole-4-carboxylic acid amide of the present invention is characterized in that the crystal provides high intensity diffraction peaks at diffraction angles ($2\theta$) in a X-ray powder diffraction spectrum of about 8.623, 12.121, 17.298, 23.397, 23.944, 24.119, 24.873, 25.948, and 28.821.

The hydrobromide salt of 3-(4-bromo-2,6-difluoro-benzyloxy)-5-[3-(4-pyrrolidin-1-yl-butyl)-ureido]-isothiazole-4-carboxylic acid amide of the present invention is characterized in that the crystal provides high intensity diffraction peaks at diffraction angles ($2\theta$) in a X-ray powder diffraction spectrum of about 8.687, 12.264, 17.374, 23.711, 24.335, and 25.769.

The hemi-citrate salt of 3-(4-bromo-2,6-difluoro-benzyloxy)-5-[3-(4-pyrrolidin-1-yl-butyl)-ureido]-isothiazole-4-carboxylic acid amide of the present invention is characterized in that the crystal provides high intensity diffraction peaks at diffraction angles ($2\theta$) in a X-ray powder diffraction spectrum of about 4.306, 16.317, 20.988, 21.476, 22.643, 23.384, 24.891, 27.573, and 27.840.

The acetate salt of 3-(4-bromo-2,6-difluoro-benzyloxy)-5-[3-(4-pyrrolidin-1-yl-butyl)-ureido]-isothiazole-4-carboxylic acid amide of the present invention is characterized in that the crystal provides high intensity diffraction peaks at diffraction angles ($2\theta$) in a X-ray powder diffraction spectrum of about 6.096, 12.183, 17.451, 18.288, 22.441, 23.086, and 24.439.

The p-tosylate salt of 3-(4-bromo-2,6-difluoro-benzyloxy)-5-[3-(4-pyrrolidin-1-yl-butyl)-ureido]-isothiazole-4-carboxylic acid amide of the present invention is characterized in that the crystal provides high intensity diffraction peaks at diffraction angles ($2\theta$) in a X-ray powder diffraction spectrum of about 20.446, 20.760, 22.092, 22.371, 23.190, and 26.239.

The L-tartrate salt of 3-(4-bromo-2,6-difluoro-benzyloxy)-5-[3-(4-pyrrolidin-1-yl-butyl)-ureido]-isothiazole-4-carboxylic acid amide of the present invention is characterized in that the crystal provides high intensity diffraction peaks at diffraction angles ($2\theta$) in a X-ray powder diffraction spectrum of about 4.061, 20.821, 21.634, 22.179 and 25.858.

The hemi-succinate (Form A) salt of 3-(4-bromo-2,6-difluoro-benzyloxy)-5-[3-(4-pyrrolidin-1-yl-butyl)-ureido]-isothiazole-4-carboxylic acid amide of the present invention is characterized in that the crystal provides high intensity diffraction peaks at diffraction angles ($2\theta$) in a X-ray powder diffraction spectrum of about 4.634, 16.735, 22.179, and 25.002. Form A hemi-succinate absorbs 0.6% water at 90% relative humidity.

The hemi-succinate (Form B) salt of 3-(4-bromo-2,6-difluoro-benzyloxy)-5-[3-(4-pyrrolidin-1-yl-butyl)-ureido]-isothiazole-4-carboxylic acid amide of the present invention is characterized in that the crystal provides high intensity diffraction peaks at diffraction angles ($2\theta$) in a X-ray powder diffraction spectrum of about 6.714, 15.272, 19.197, 19.457, 24.487, and 24.802. Form B hemi-succinate absorbs 1.5% water at 90% relative humidity.

The mesylate salt of 3-(4-bromo-2,6-difluoro-benzyloxy)-5-[3-(4-pyrrolidin-1-yl-butyl)-ureido]-isothiazole-4-carboxylic acid amide of the present invention is characterized in that the crystal provides high intensity diffraction peaks at diffraction angles ($2\theta$) in a X-ray powder diffraction spectrum of about 4.417, 17.288, 20.828, 21.677, 22.148, 25.427, and 27.006.

The in vitro activity of the compounds of formula I in inhibiting the KDR/VEGF receptor may be determined by the following procedure.

The ability of the compounds of the present invention to inhibit tyrosine kinase activity may be measured using a recombinant enzyme in an assay that measures the ability of compounds to inhibit the phosphorylation of the exogenous substrate, polyGluTyr (PGT, Sigma™, 4:1). The kinase domain of the human KDR/VEGF receptor (amino acids 805–1350) is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (0.625 $\mu$g PGT per well). Test compounds are diluted in dimethylsulfoxide (DMSO), and then added to the PGT plates so that the final concentration of DMSO in the assay is 1.6% (v/v). The recombinant enzyme is diluted in phosphorylation buffer (50 mM Hepes, pH 7.3, 125 mM NaCl, 24 mM $MgCl_2$). The reaction is initiated by the addition of ATP to a final concentration of 10 $\mu$M. After a 30 minute incubation at room temperature with shaking, the reaction is aspirated, and the plates are washed with wash buffer (PBS-containing 0.1% Tween-20). The amount of phosphorylated PGT is quantitated by incubation with a HRP-conjugated (HRP is horseradish peroxidase) PY-54 antibody (Transduction Labs), developed with TMB peroxidase (TMB is 3,3',5,5'-tetramethylbenzidine), and the reaction is quantitated on a BioRad™ Microplate reader at 450 nM. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit KDR tyrosine kinase activity for the full length protein that exists in a cellular context, the porcine aortic endothelial (PAE) cells transfected with the human KDR (Waltenberger et al., J. Biol. Chem. 269:26988, 1994) may be used. Cells are plated and allowed to attach to 96-well dishes in the same media (Ham's F12) with 10% v/v FBS (fetal bovine serum). The cells are then washed, re-fed with serum depleted media (0.1% v/v FBS) that contains 0.1% (v/v) bovine serum albumin (BSA), and allowed to incubate for 16–24 hours. Immediately prior to dosing with compound, the cells are re-fed with the serum depleted media (0.1% v/v FBS) (without BSA). Test compounds, dissolved in DMSO, are diluted into the media (final DMSO concentration 0.5%

(v/v)). At the end of a 2 hour incubation, $VEGF_{165}$ (50 ng/ml final) is added to the media for an 8 minute incubation. The cells are washed and lysed in 50μ lysis buffer containing 20 mM Tris-HCL (pH 8), 150 mM NaCl, 1% v/v NP40, 2 mM $NaVO_4$, 500 μM EDTA, 1 mM PMSF, and 1 tablet/25 ml EDTA free complete® Protease Inhibitor Table, Roche. The cell lysates is then diluted to a final volume of 150 μl in PBS/1 mM $NaVO_4$. The extent of phosphorylation of KDR is measured using an ELISA assay. Reactibind Goat-anti Rabbit plates (Pierce) are blocked with Superblock buffer (Pierce) prior to addition of the anti-flk-1 C-20 antibody (0.5 μg per well, Santa Cruz). Any unbound antibody is washed off the plates prior to addition of 100 μl cell lysate. After a 2 hour incubation of the lysates with the flk-1 antibody, the KDR associated phosphotyrosine is quantitated by development with the HRP-conjugated PY-54 antibody and TMB, as described above. The ability of the compounds to inhibit the VEGF-stimulated autophosphorylation reaction by 50%, relative to VEGF-stimulated controls is reported as the $IC_{50}$ value for the test compound.

The ability of the compounds to inhibit mitogenesis in human endothelial cells is measured by their ability to inhibit $^3$H-thymidine incorporation into HUVE cells (human umbilical vein endothelial cells, Clonetics™). This assay has been well described in the literature (Waltenberger J et al. J. Biol. Chem. 269: 26988, 1994; Cao Y et al. J. Biol. Chem. 271: 3154, 1996). Briefly, $10^4$ cells are plated in collagen-coated 24-well plates and allowed to attach. Cells are re-fed in serum-free media, and 24 hours later are treated with various concentrations of compound (prepared in DMSO, final concentration of DMSO in the assay is 0.2% v/v), and 2–30 ng/ml $VEGF_{165}$. During the last 3 hours of the 24 hour compound treatment, the cells are pulsed with $^3$H thymidine (NEN, 1 μCi per well). The media are then removed, and the cells washed extensively with ice-cold Hank's balanced salt solution, and then 2 times with ice cold trichloroacetic acid (10% v/v). The cells are lysed by the addition of 0.2 ml of 0.1 N NaOH, and the lysates transferred into scintillation vials. The wells are then washed with 0.2 ml of 0.1 N HCl, and this wash is then transferred to the vials. The extent of $^3$H thymidine incorporation is measured by scintillation counting. The ability of the compounds to inhibit incorporation by 50%, relative to control (VEGF treatment with DMSO vehicle only) is reported as the $IC_{50}$ value for the test compound.

The activity of the compounds of formula 1 in vivo, can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", *Cancer Res.*, 35, 2434–2439 (1975) and Corbett, T. H., et al., "A Mouse Colon-tumor Model for Experimental Therapy", *Cancer Chemother. Rep.* (Part 2)", 5, 169–186 (1975), with slight modifications. Tumors are induced in the left flank by s.c. injection of $1 \times 10^6$ log phase cultured tumor cells (human MDA-MB-468 breast or human HN5 head and neck carcinoma cells) suspended in 0.10 ml RPMI 1640. After sufficient time has elapsed for the tumors to become palpable (2–3 mm in diameter) the test animals (athymic mice) are treated with active compound (formulated by dissolution in DMSO typically at a concentration of 50 to 100 mg/mL followed by 1:9 dilution into saline or, alternatively, 1:9 dilution into 0.1% Pluronic™ P105 in 0.9% saline) by the intraperitoneal (ip) or oral (po) routes of administration twice daily (i.e., every 12 hours) for 5 consecutive days. In order to determine an anti-tumor effect, the tumor is measured in millimeters with Vernier calipers across two diameters and the tumor size (mg) is calculated using the formula: Tumor weight=(length×[width]$^2$)/2, according to the methods of Geran, R. I., et al. "Protocols for Screening Chemical Agents and Natural Products Against Animal Tumors and Other Biological Systems", Third Edition, *Cancer Chemother. Rep.*, 3, 1–104 (1972). Results are expressed as percent inhibition, according to the formula: Inhibition (%)=($TuW_{control}$−$TuW_{test}$)$TuW_{control}$×100%. The flank site of tumor implantation provides reproducible dose/response effects for a variety of chemotherapeutic agents, and the method of measurement (tumor diameter) is a reliable method for assessing tumor growth rates.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; antimetabolites, for example 5-fluorouracil, cytosine arabinoside and hydroxyurea, or, for example, one of the preferred anti-metabolites disclosed in European Patent Application No. 239362 such as N-(5[-N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations.

The spectrums in FIGS. 1–9 were recorded using a Siemens θ/2θ powder diffractometer equipped as follows: forty position autosampler, goniometer with fixed slits, sealed-tude copper (Cu) X-ray source (wavelength 1: 1.54056, wavelength 2: 1.54439), and Kevex solid state detector. Tube power: 40-mA×50-kV, or as appropriate. Slits: 1×1×0.6 mm (source, anti-scatter, and detector slits, respectively). Step size: 0.04 degrees in 2T. Time per step: 1 second. Scan start: 3 degrees in 2T. Scan stop: 40 degrees in 2T.

EXAMPLE 1

Free Base of 3-(4-bromo-2,6-difluoro-benzyloxy)-5-[3-(4-pyrrolidin-1-yl-butyl)-ureido]-isothiazole-4-carboxylic Acid The free base of 3-(4-bromo-2,6-difluoro-benzyloxy)-5-[3-(4-pyrrolidin-1-yl-butyl)-ureido]-isothiazole-4-carboxylic acid is prepared according to the procedure described in Example 30 of U.S. Ser. No. 09/316837, filed May 21, 1999, the disclosure of which is hereby incorporated herein by reference in its entirety. Mp 208° C. (DSC). Characteristic X-ray powder diffraction peaks (2-theta, [% relative intensity]): 9.314 [100.0], 11.356 [44.8], 15.897 [49.6], 22.059 [84.5], 22.520 [63.3], 22.726 [70.0], 23.927 [67.6], 24.307 [60.5], 25.310 [64.8], and 26.551 [86.6].

EXAMPLE 2

Hydrochloride Salt of 3-(4-bromo-2,6-difluoro-benzyloxy)-5-[3-(4-pyrrolidin-1-yl-butyl)-ureido]-isothiazole-4-carboxylic Acid Amide 3-(4-bromo-2,6-difluoro-benzyloxy)-5-[3-(4-pyrrolidin-1-yl-butyl)-ureido]-isothiazole-4-carboxylic acid amide (500 mg, 0.939 mmol) was dissolved in EtOH (20 mL) at reflux, allowed to cool to ambient temperature and treated with HCl (0.94 mL of a 1.0 M solution in Et$_2$O) while swirling flask. The mixture was then shaken gently with heating at 50° C. for 3 hours and at ambient temperature for 3 days. The solid was filtered, dried under high vacuum to afford a white solid (468 mg, 0.823 mmol, 82%). Melting point 230° C. (DSC). Hygroscopicity: 1% (by weight)) at 90% relative humidity at ambient temperature (RH). Characteristic X-ray powder diffraction peaks (2-theta, [% relative intensity]): 8.623 [90.7], 12.121 [38.9], 17.298 [95.2], 23.397 [44.7], 23.944 [51.7], 24.119 [62.7], 24.873 [55.7], 25.948 [100], and 28.821 [39.6].

EXAMPLE 3

Hydrobromide Salt of 3-(4-bromo-2,6-difluoro-benzyloxy)-5-[3-(4-pyrrolidin-1-yl-butyl)-ureido]-isothiazole-4-carboxylic Acid Hydrobromic acid (1.0 mL of 47–49% aqueous 8.9 M solution) was added to ~4 mL of MeOH and then filled to the 8.9 mL mark with MeOH in a graduated cylinder. Separately, 3-(4-bromo-2,6-difluoro-benzyloxy)-5-[3-(4-pyrrolidin-1-yl-butyl)-ureido]-isothiazole-4-carboxylic acid (500 mg, 0.939 mmol) was dissolved in CH$_2$Cl$_2$ (10 mL) and MeOH (4 mL) and treated with HBr (1.0 mL of the solution described above). This solution was then placed in a diffusion chamber surrounded with Et$_2$O. After 16 hours, solid was present. The Et$_2$O was replaced by fresh Et$_2$O and the diffusion continued overnight. A white solid (529 mg, 0.863 mmol, 86%) was obtained. Melting point 201.0° C. (DSC). Hygroscopicity: 0.1% at 87% relative RH. Characteristic X-ray powder diffraction peaks (2-theta, [% relative intensity]): 8.687 [100.0], 12.264 [35.9], 17.374 [42.3], 23.711 [24.0], 24.335 [20.7], and 25.769 [34.3].

EXAMPLE 4

Hemi-Citrate Salt of 3-(4-bromo-2,6-difluoro-benzyloxy)-5-[3-(4-pyrrolidin-1-yl-butyl)-ureido]-isothiazole-4-carboxylic Acid 3-(4-bromo-2,6-difluoro-benzyloxy)-5-[3-(4-pyrrolidin-1-yl-butyl )-ureido]-isothiazole-4-carboxylic acid (532 mg, 1.00 mmol), citric acid (96 mg, 0.50 mmol), and MeOH (8 mL) were combined in a 16 mL vial with a septum top and heated, with shaking, at 75° C. for 24 hours. The mixture was cooled to ambient temperature and filtered. The solid was washed with MeOH and dried by continued passage of air through the solid. A white solid (530 mg, 0.843 mmol, 84%) was obtained. Melting point 201.7° C. (DSC). Hygroscopicity: 0.43% at 87% relative RH. Characteristic X-ray powder diffraction peaks (2-theta, [% relative intensity]): 4.306 [79.9], 16.317 [100.0], 20.988 [32.7], 21.476 [30.9], 22.643 [48.7], 23.384 [76.9], 24.891 [76.0], 27.573 [47.9], and 27.840 [32.3].

EXAMPLE 5

Acetate Salt of 3-(4-bromo-2,6-difluoro-benzyloxy)-5-[3-(4-pyrrolidin-1-yl-butyl)-ureido]-isothiazole-4-carboxylic Acid 3-(4-bromo-2,6-difluoro-benzyloxy)-5-[3-(4-pyrrolidin-1-yl-butyl)-ureido]-isothiazole-4-carboxylic acid (532 mg, 1.00 mmol), acetic acid (57 μL, 1.0 mmol), and MeOH (3 mL) were combined in a 8 mL vial with a septum top and heated, with shaking, at 75° C. for 24 hours. The mixture was cooled to ambient temperature and placed in a chamber with Et$_2$O. After five hours large crystals were harvested by decanting liquid and washing the solid with MeOH and then $Et_2O$. The solid was dried by brief passage of air through the solid. A white solid (330 mg, 0.557 mmol, 56%) was obtained. Melting point 175° C. (DSC). Characteristic X-ray powder diffraction peaks (2-theta, [% relative intensity]): 6.096 [21.7], 12.183 [21.4], 17.451 [33.3], 18.288 [100.0], 22.441 [57.7], 23.086 [19.9], and 24.439 [20.7].

EXAMPLE 6 p-Tosylate Salt of 3-(4-bromo-2,6-difluoro-benzyloxy)-5-[3-(4-pyrrolidin-1-yl-butyl)-ureido]-isothiazole-4-carboxylic Acid 3-(4-bromo-2,6-difluoro-benzyloxy)-5-[3-(4-pyrrolidin-1-yl-butyl )-ureido]-isothiazole-4-carboxylic acid (532 mg, 1.00 mmol), p-toluenesulfonic acid monohydrate (179 mg, 1.00 mmol), MeOH (10 mL), and $CH_2Cl_2$ (1 mL) were combined and filtered to remove small amount of very fine particulate and washed through with additional $CH_2Cl_2$ (3 mL). The solution was added to additional $CH_2Cl_2$ (4 mL) plus MeOH (1 mL) and placed in a diffusion chamber with $Et_2O$ overnight. No crystals were formed so the $Et_2O$ was replaced by pentane overnight. The solid was washed with $Et_2O$ and dried by continued passage of air through the solid. A white solid (572 mg, 0.812 mmol, 81%) was obtained. Melting Point 140 and 174° C. (DSC). Hygroscopicity: −0.9% at 87% relative RH. Characteristic X-ray powder diffraction peaks (2-theta, [% relative intensity]): 20.446 [100.0], 20.760 [74.0], 22.092 [81.7], 22.371 [70.8], 23.190 [65.2], 26.239 [61.5].

EXAMPLE 7

L-Tartrate Salt of 3-(4-bromo-2,6-difluoro-benzyloxy)-5-[3-(4-pyrrolidin-1-yl-butyl)-ureido]-isothiazole-4-carboxylic Acid 3-(4-bromo-2,6-difluoro-benzyloxy)-5-[3-(4-pyrrolidin-1-yl-butyl)-ureido]-isothiazole-4-carboxylic acid (532 mg, 1.00 mmol), L-tartaric acid (150 mg, 1.00 mmol), and MeOH (8 mL) were combined in a 16 mL vial with a septum top and heated, with shaking, at 75° C. for 24 hours. The mixture was cooled to ambient temperature and filtered. The solid was washed with MeOH and dried by continued passage of air through the solid. A white solid (617 mg, 0.904 mmol, 90%) was obtained. Melting point 206° C. (DSC). Hygroscopicity: 0.3% at 100% RH. Characteristic X-ray powder diffraction peaks (2-theta, [% relative intensity]): 4.061 [82.9], 20.821 [85.6], 21.634 [100.0], 22.179 [94.0], 25.858 [95.1].

EXAMPLE 8

Hemi-Succinate Salt of 3-(4-bromo-2,6-difluoro-benzyloxy)-5-[3-(4-pyrrolidin-1-yl-butyl)-ureido]-isothiazole-4-carboxylic Acid (Form A)

3-(4-bromo-2,6-difluoro-benzyloxy)-5-[3-(4-pyrrolidin-1-yl-butyl)-ureido]-isothiazole-4-carboxylic acid (532 mg, 1.00 mmol), succinic acid (59 mg, 0.50 mmol), and MeOH (8 mL) were combined in a 16 mL vial with a septum top and heated, with shaking, at 75° C. for 24 hours. The mixture was cooled to ambient temperature and filtered. The solid was washed with MeOH and dried by continued passage of air through the solid. A white solid (500 mg, 0.845 mmol, 85%) was obtained. Melting point Form A 216° C. (DSC). Hygroscopicity: 0.6% at 90% relative RH. Characteristic X-ray powder diffraction peaks (2-theta, [% relative intensity]): Form A: 4.634 [100.0], 16.735 [67.2], 22.179 [60.8], and 25.002 [70.3].

EXAMPLE 9

Hemi-Succinate Salt of 3-(4-bromo-2,6-difluoro-benzyloxy)-5-[3-(4-pyrrolidin-1-yl-butyl)-ureido]-isothiazole-4-carboxylic Acid (Form B)

3-(4-bromo-2,6-difluoro-benzyloxy)-5-[3-(4-pyrrolidin-1-yl-butyl)-ureido]-isothiazole-4-carboxylic acid (100 mg) was dissolved with heat in 6 mL EtOH:MeOH (2:1). Succinic acid (11.1 mg, 0.5 eq) dissolved in EtOH was added to the former solution. The mixture was allowed to cool to ambient temperature and stirred for 20 min. The solid was filtered, washed with EtOH, and dried by continued passage of air through the solid. A white solid (80 mg, 70%) was obtained. Hygroscopicity Form B: 1.5% at 90% relative RH. Characteristic X-ray powder diffraction peaks (2-theta, [% relative intensity]): 6.714 [31.0], 15.272 [100.0], 19.197 [59.3], 19.457 [50.0], 24.487 [99.0], and 24.802 [79.1].

EXAMPLE 10

Mesylate Salt of 3-(4-bromo-2,6-difluoro-benzyloxy)-5-[3-(4-pyrrolidin-1-yl-butyl)-ureido]-isothiazole-4-carboxylic Acid 3-(4-bromo-2,6-difluoro-benzyloxy)-5-[3-(4-pyrrolidin-1-yl-butyl)-ureido]-isothiazole-4-carboxylic acid (10.9 g, 20.5 mmol) was dissolved in MeOH (150 mL) and cooled to 0° C. In a separate flask, $H_3CSO_3H$ (1.33 mL) was added to MeOH (15 mL) at 0° C. The acid solution was then added dropwise over 10 minutes to the amine starting material solution. The solution was warmed to ambient temperature, filtered to remove minor solid impurities, diluted with $Et_2O$ (1 L) and stirred for 1 h. The mixture was further diluted with hexane (500 mL) and cooled to 0° C. with continued stirring. After setting overnight at 0° C., the crystals were filtered, washed with hexane, and sucked dry to afford a white solid (11.1 g, 17.7 mmol, 86%). Characteristic X-ray powder diffraction peaks (2-theta, [% relative intensity]): 4.417 [99.3], 17.288 [45.5], 20.828 [39.6], 21.677 [43.5], 22.148 [68.3], 25.427 [100.0], and 27.006 [37.5].

What is claimed is:

1. A hydrobromide salt of 3-(4-bromo-2,6-difluoro-benzyloxy)-5-[3-(4-pyrrolidin-1-yl-butyl)-ureido]-isothiazole-4-carboxylic acid amide.

2. The salt according to claim 1, wherein said salt has a X-ray powder diffraction spectrum substantially the same as the X-ray powder diffraction spectrum shown in FIG. 2.

3. The salt according to claim 2, which provides high-intensity diffraction peaks at diffraction angles (2θ) of 8.687, 12.264, 17.374, 23.711, 24.335, and 25.769 in the X-ray powder diffraction analysis.

4. A hydrobromide salt of 3-(4-bromo-2,6-difluoro-benzyloxy)-5-[3-(4-pyrrolidin-1-yl-butyl)-ureido]-isothiazole-4-carboxylic acid amide that exhibits an X-ray powder diffraction spectrum having characteristic peaks expressed in degrees (2θ) at approximately:

| 2θ | RI (%) |
| --- | --- |
| 3.156 | 2.5 |
| 4.615 | 2.4 |
| 6.331 | 9.3 |
| 8.687 | 100.0 |
| 12.264 | 35.9 |
| 12.890 | 2.2 |
| 13.445 | 1.4 |
| 14.140 | 3.4 |

-continued

| 2θ | RI (%) |
|---|---|
| 16.083 | 4.0 |
| 17.374 | 42.3 |
| 17.767 | 5.6 |
| 18.185 | 3.2 |
| 18.913 | 16.6 |
| 19.528 | 9.5 |
| 20.286 | 2.5 |
| 20.581 | 2.9 |
| 21.874 | 13.6 |
| 23.188 | 5.6 |
| 23.711 | 24.0 |
| 24.335 | 20.7 |
| 25.435 | 9.1 |
| 25.769 | 34.3 |
| 26.940 | 4.1 |
| 27.345 | 7.0 |
| 28.160 | 5.7 |
| 28.528 | 6.1 |
| 28.916 | 9.4 |
| 29.418 | 7.7 |
| 30.266 | 4.6 |
| 31.561 | 3.9 |
| 32.082 | 3.4 |
| 32.638 | 5.3 |
| 32.925 | 4.4 |
| 33.256 | 3.7 |
| 33.897 | 7.9 |
| 34.628 | 2.8 |
| 34.999 | 3.3 |
| 35.432 | 6.1 |
| 36.006 | 4.3 |
| 37.361 | 3.4 |
| 38.224 | 4.8 |

5. A hemi-citrate salt of 3-(4-bromo-2,6-difluoro-benzyloxy)-5-[3-(4-pyrrolidin-1-yl-butyl)-ureido]-isothiazole-4-carboxylic acid amide.

6. The salt according to claim 5, wherein said salt has a X-ray powder diffraction spectrum substantially the same as the X-ray powder diffraction spectrum shown in FIG. 3.

7. The salt according to claim 6, which provides high-intensity diffraction peaks at diffraction angles (2θ) of 4.306, 16.317, 20.988, 21.476, 22.643, 23.384, 24.891, 27.573, and 27.840 in the X-ray powder diffraction analysis.

8. A hemi-citrate salt of 3-(4-bromo-2,6-difluoro-benzyloxy)-5-[3-(4-pyrrolidin-1-yl-butyl)-ureido]-isothiazole-4-carboxylic acid amide that exhibits an X-ray powder diffraction spectrum having characteristic peaks expressed in degrees (2θ) at approximately:

| 2θ | RI (%) |
|---|---|
| 3.201 | 14.3 |
| 4.306 | 79.9 |
| 6.429 | 7.0 |
| 8.620 | 6.0 |
| 9.589 | 5.6 |
| 10.583 | 6.8 |
| 11.449 | 20.9 |
| 12.300 | 8.7 |
| 13.766 | 12.4 |
| 14.086 | 7.0 |
| 14.710 | 9.5 |
| 15.297 | 16.0 |
| 16.317 | 100.0 |
| 17.309 | 14.4 |
| 17.572 | 16.5 |
| 18.258 | 13.7 |
| 18.693 | 15.8 |
| 19.344 | 23.4 |

-continued

| 2θ | RI (%) |
|---|---|
| 20.394 | 16.4 |
| 20.988 | 32.7 |
| 21.476 | 30.9 |
| 21.994 | 27.3 |
| 22.643 | 48.7 |
| 23.384 | 76.9 |
| 24.217 | 28.8 |
| 24.891 | 76.0 |
| 25.320 | 20.4 |
| 25.948 | 28.0 |
| 26.370 | 25.7 |
| 27.573 | 47.9 |
| 27.840 | 32.3 |
| 28.609 | 19.6 |
| 29.630 | 17.4 |
| 31.251 | 14.6 |
| 31.848 | 14.2 |
| 32.235 | 11.8 |
| 34.147 | 11.0 |
| 35.878 | 16.2 |
| 37.337 | 12.3 |

9. An acetate salt of 3-(4-bromo-2,6-difluoro-benzyloxy)-5-[3-(4-pyrrolidin-1-yl-butyl)-ureido]-isothiazole-4-carboxylic acid amide.

10. The salt according to claim 9, wherein said salt has a X-ray powder diffraction spectrum substantially the same as the X-ray powder diffraction spectrum shown in FIG. 4.

11. The salt according to claim 10, which provides high-intensity diffraction peaks at diffraction angles (2θ) of 6.096, 12.183, 17.451, 18.288, 22.441, 23.086, and 24.439 in the X-ray powder diffraction analysis.

12. A acetate salt of 3-(4-bromo-2,6-difluoro-benzyloxy)-5-[3-(4-pyrrolidin-1-yl-butyl)-ureido]-isothiazole-4-carboxylic acid amide that exhibits an X-ray powder diffraction spectrum having characteristic peaks expressed in degrees (2θ) at approximately:

| 2θ | RI (%) |
|---|---|
| 6.096 | 21.7 |
| 8.625 | 2.8 |
| 11.840 | 2.9 |
| 12.183 | 21.4 |
| 14.836 | 4.2 |
| 15.264 | 9.2 |
| 15.824 | 5.0 |
| 16.793 | 4.5 |
| 17.121 | 12.8 |
| 17.451 | 33.3 |
| 17.920 | 8.7 |
| 18.288 | 100.0 |
| 20.088 | 3.6 |
| 20.458 | 11.3 |
| 21.346 | 8.9 |
| 22.441 | 57.7 |
| 23.086 | 19.9 |
| 24.038 | 7.5 |
| 24.439 | 20.7 |
| 24.760 | 11.3 |
| 25.861 | 5.0 |
| 27.930 | 5.8 |
| 28.820 | 10.0 |
| 29.648 | 6.1 |
| 30.634 | 3.3 |
| 31.112 | 3.2 |
| 31.951 | 2.9 |
| 32.271 | 4.1 |
| 33.127 | 5.1 |
| 35.030 | 3.4 |

-continued

| 2θ | RI (%) |
|---|---|
| 36.445 | 3.2 |
| 37.830 | 3.0 |
| 39.478 | 2.5 |

13. A p-tosylate salt of 3-(4-bromo-2,6-difluoro-benzyloxy)-5-[3-(4-pyrrolidin-1-yl-butyl)-ureido]-isothiazole-4-carboxylic acid amide.

14. The salt according to claim 13, wherein said salt has a X-ray powder diffraction spectrum substantially the same as the X-ray powder diffraction spectrum shown in FIG. 5.

15. The salt according to claim 14, which provides high-intensity diffraction peaks at diffraction angles (2θ) of 20.446, 20.760, 22.092, 22.371, 23.190, and 26.239 in the X-ray powder diffraction analysis.

16. A p-tosylate salt of 3-(4-bromo-2,6-difluoro-benzyloxy)-5-[3-(4-pyrrolidin-1-yl-butyl)-ureido]-isothiazole-4-carboxylic acid amide that exhibits an X-ray powder diffraction spectrum having characteristic peaks expressed in degrees (2θ) at approximately:

| 2θ | RI (%) |
|---|---|
| 6.817 | 50.3 |
| 7.515 | 28.0 |
| 7.822 | 22.3 |
| 11.157 | 15.0 |
| 12.205 | 24.5 |
| 12.800 | 30.0 |
| 13.047 | 43.6 |
| 13.373 | 53.9 |
| 14.337 | 18.3 |
| 15.001 | 22.2 |
| 15.601 | 21.4 |
| 16.297 | 14.0 |
| 16.943 | 32.0 |
| 17.362 | 23.5 |
| 18.174 | 21.3 |
| 18.976 | 40.4 |
| 19.739 | 36.7 |
| 20.446 | 100.0 |
| 20.760 | 74.0 |
| 22.092 | 81.7 |
| 22.371 | 70.8 |
| 23.190 | 65.2 |
| 24.110 | 30.5 |
| 25.471 | 40.2 |
| 25.932 | 50.4 |
| 26.239 | 61.5 |
| 27.355 | 48.8 |
| 27.833 | 39.0 |
| 28.167 | 34.5 |
| 29.672 | 19.6 |
| 31.038 | 19.3 |
| 31.586 | 21.2 |
| 35.357 | 19.6 |
| 36.800 | 16.4 |

17. A L-tartrate salt of 3-(4-bromo-2,6-difluoro-benzyloxy)-5-[3-(4-pyrrolidin-1-yl-butyl)-ureido]-isothiazole-4-carboxylic acid amide.

18. The salt according to claim 17, wherein said salt has a X-ray powder diffraction spectrum substantially the same as the X-ray powder diffraction spectrum shown in FIG. 6.

19. The salt according to claim 18, which provides high-intensity diffraction peaks at diffraction angles (2θ) of 4.061, 20.821, 21.634, 22.179, and 25.858 in the X-ray powder diffraction analysis.

20. A L-tartrate salt of 3-(4-bromo-2,6-difluoro-benzyloxy)-5-[3-(4-pyrrolidin-1-yl-butyl)-ureido]-isothiazole-4-carboxylic acid amide that exhibits an X-ray powder diffraction spectrum having characteristic peaks expressed in degrees (2θ) at approximately:

| 2θ | RI (%) |
|---|---|
| 4.061 | 82.9 |
| 6.678 | 11.8 |
| 8.057 | 29.4 |
| 9.383 | 8.7 |
| 10.647 | 8.3 |
| 11.711 | 60.2 |
| 12.075 | 27.4 |
| 12.868 | 33.8 |
| 13.320 | 22.7 |
| 14.631 | 27.2 |
| 15.428 | 22.7 |
| 16.143 | 31.2 |
| 16.853 | 65.3 |
| 17.338 | 56.2 |
| 18.400 | 97.0 |
| 18.639 | 98.2 |
| 18.994 | 52.4 |
| 19.722 | 42.9 |
| 20.010 | 53.0 |
| 20.334 | 58.7 |
| 20.821 | 85.6 |
| 21.634 | 100.0 |
| 22.179 | 94.0 |
| 22.730 | 73.8 |
| 23.477 | 77.1 |
| 24.257 | 67.8 |
| 24.788 | 53.8 |
| 25.081 | 60.9 |
| 25.858 | 95.1 |
| 26.803 | 59.6 |
| 28.386 | 34.3 |
| 29.067 | 34.1 |
| 29.844 | 30.5 |
| 31.309 | 39.4 |
| 32.465 | 36.1 |
| 33.442 | 33.7 |
| 34.090 | 34.6 |
| 34.642 | 26.8 |
| 35.635 | 33.7 |
| 36.073 | 28.5 |
| 36.771 | 24.5 |
| 38.080 | 22.6 |

21. A hemi-succinate salt of 3-(4-bromo-2,6-difluoro-benzyloxy)-5-[3-(4-pyrrolidin-1-yl-butyl)-ureido]-isothiazole-4-carboxylic acid amide which is Form A.

22. The salt according to claim 21, wherein said salt has a X-ray powder diffraction spectrum substantially the same as the X-ray powder diffraction spectrum shown in FIG. 7.

23. The salt according to claim 22, which provides high-intensity diffraction peaks at diffraction angles (2θ) of 4.634, 16.735, 22.179, and 25.002 in the X-ray powder diffraction analysis.

24. A hemi-succinate form A salt of 3-(4-bromo-2,6-difluoro-benzyloxy)-5-[3-(4-pyrrolidin-1-yl-butyl)-ureido]-isothiazole-4-carboxylic acid amide that exhibits an X-ray powder diffraction spectrum having characteristic peaks expressed in degrees (2θ) at approximately:

| 2θ | RI (%) |
|---|---|
| 4.634 | 100.0 |
| 6.149 | 15.5 |
| 9.843 | 6.2 |
| 11.392 | 11.3 |
| 11.937 | 19.2 |

-continued

| 2θ | RI (%) |
| --- | --- |
| 13.683 | 13.8 |
| 14.440 | 13.5 |
| 14.896 | 21.9 |
| 15.996 | 14.4 |
| 16.735 | 67.2 |
| 17.760 | 20.6 |
| 18.679 | 18.4 |
| 19.421 | 30.2 |
| 20.586 | 29.2 |
| 22.179 | 60.8 |
| 22.866 | 38.7 |
| 23.255 | 39.5 |
| 24.079 | 44.6 |
| 25.002 | 70.3 |
| 26.549 | 26.8 |
| 27.609 | 23.7 |
| 30.106 | 14.3 |
| 30.797 | 13.7 |
| 37.769 | 11.4 |

25. A hemi-succinate salt of 3-(4-bromo-2,6-difluoro-benzyloxy)-5-[3-(4-pyrrolidin-1-yl-butyl)-ureido]-isothiazole-4-carboxylic acid amide which is Form B.

26. The salt according to claim 25, wherein said salt has a X-ray powder diffraction spectrum substantially the same as the X-ray powder diffraction spectrum shown in FIG. 8.

27. The salt according to claim 26, which provides high-intensity diffraction peaks at diffraction angles (2θ) of 6.714, 15.272, 19.197, 19.457, 24.487, and 24.802 in the X-ray powder diffraction analysis.

28. A hemi-succinate form B salt of 3-(4-bromo-2,6-difluoro-benzyloxy)-5-[3-(4-pyrrolidin-1-yl-butyl)-ureido]-isothiazole-4-carboxylic acid amide that exhibits an X-ray powder diffraction spectrum having characteristic peaks expressed in degrees (2θ) at approximately:

| 2θ | RI (%) |
| --- | --- |
| 6.714 | 31.0 |
| 8.666 | 7.3 |
| 11.092 | 8.6 |
| 11.696 | 21.9 |
| 12.008 | 15.9 |
| 12.630 | 7.3 |
| 13.466 | 17.2 |
| 13.774 | 13.9 |
| 15.272 | 100.0 |
| 15.813 | 19.8 |
| 16.551 | 17.5 |
| 16.875 | 26.4 |
| 17.365 | 12.6 |
| 17.986 | 8.6 |
| 18.710 | 26.4 |
| 19.197 | 59.3 |
| 19.457 | 50.0 |
| 20.597 | 17.2 |
| 21.160 | 28.8 |
| 21.648 | 21.7 |
| 22.988 | 15.0 |
| 23.568 | 18.6 |
| 24.487 | 99.0 |
| 24.802 | 79.1 |
| 25.640 | 15.9 |
| 26.641 | 20.1 |
| 27.090 | 15.1 |
| 27.843 | 21.5 |
| 28.552 | 19.7 |
| 29.732 | 14.1 |
| 30.796 | 17.5 |
| 33.484 | 9.4 |
| 34.594 | 11.4 |
| 37.212 | 15.5 |
| 37.905 | 8.9 |
| 39.023 | 8.9 |

29. A method of treating a hyperproliferative disorder in a mammal which comprises administering to the mammal a therapeutically effective amount of a compound according to claim 1.

30. The method of claim 29 wherein the method is for the treatment of a cancer selected from brain, squamous cell, bladder, gastric, pancreatic, breast, head, neck, oesophageal, prostate, colorectal, lung, renal, kidney, ovarian, gynecological and thyroid cancer.

31. A method for the treatment of a hyperproliferative disorder in a mammal which comprises administering to the mammal a therapeutically effective amount of a polymorph according to claim 1 in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

32. A pharmaceutical composition comprising an amount of a compound according to claim 1 effective to treat a hyperproliferative disorder in a mammal, and a pharmaceutically acceptable carrier.

33. The pharmaceutical composition of claim 32 wherein the hyperproliferative disorder is a cancer selected from brain, lung, squamous cell, bladder, gastric, pancreatic, breast, head, neck, renal, kidney, ovarian, prostate, colorectal, oesophageal, gynecological and thyroid cancer.

34. The pharmaceutical composition of claim 33, wherein the composition is adapted for oral administration.

35. The pharmaceutical composition of claim 34, wherein the pharmaceutical composition is in tablet form.

36. A method of preventing pregnancy, comprising administering to a female mammal a compound according to claim 1.

37. The method of claim 36, further comprising a pharmaceutically acceptable carrier.

* * * * *